United States Patent
Brockman et al.

(10) Patent No.: US 11,559,066 B2
(45) Date of Patent: Jan. 24, 2023

(54) REAGENTS, KITS AND METHODS FOR ASSESSING AND REDUCING RISK OF DEVELOPING CANINE HYPOTHYROIDISM AND OTHER AUTOIMMUNE CONDITIONS

(71) Applicant: Hill's Pet Nutrition, Inc., Topeka, KS (US)

(72) Inventors: Jeffrey Brockman, Lawrence, KS (US); Dennis Jewell, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 400 days.

(21) Appl. No.: 16/720,971

(22) Filed: Dec. 19, 2019

(65) Prior Publication Data

US 2021/0186059 A1    Jun. 24, 2021

(51) Int. Cl.
| | | |
|---|---|---|
| *C12Q 1/68* | (2018.01) | |
| *C07H 21/04* | (2006.01) | |
| *A23K 50/40* | (2016.01) | |
| *C12Q 1/6883* | (2018.01) | |
| *A23K 10/37* | (2016.01) | |
| *A23K 20/147* | (2016.01) | |

(52) U.S. Cl.
CPC .............. *A23K 50/40* (2016.05); *A23K 10/37* (2016.05); *A23K 20/147* (2016.05); *C12Q 1/6883* (2013.01); *C12Q 2600/156* (2013.01)

(58) Field of Classification Search
None
See application file for complete search history.

(56) References Cited

U.S. PATENT DOCUMENTS

2015/0313261 A1    11/2015    Jewell et al.

FOREIGN PATENT DOCUMENTS

| WO | 2005/051093 A1 | 6/2005 |
| WO | 2015/076832 A1 | 5/2015 |

OTHER PUBLICATIONS

Jonathan Massey (Thesis: Mapping the genes for complex canine autoimmune diseases; The university of Manchester 2012). (Year: 2012).*
Bianchi et al., 2015, "A Multi-Breed Genome-Wide Association Analysis for Canine Hypothyroidism Identifies a Shared Major Risk Locus on CFA12", Plos One, 10(8):e0134720.
International Search Report and the Written Opinion of the International Searching Authority issued in International Application PCT/US2019/067481 dated Jun. 25, 2020.
Kennedy et al., 2006, "Association of Canine Hypothyroidism with a Common Major Histocompatibility Complex DLA Class II Allele", Tissue Antigens, 68(1):82-86.

* cited by examiner

*Primary Examiner* — Jeanine A Goldberg

(57) ABSTRACT

Methods of analyzing a biological sample obtained from the canine subject for the presence of one or two copies one or two copies of minor allele T of SNP Affx-206229307; or one or two copies of minor allele A of SNP Affx-206560187; or one or two copies of minor allele T of SNP Affx-206229307 and one or two copies of minor allele A of SNP Affx-206560187 are disclosed. The methods are used in methods to identify a canine subject that has an increased likelihood or risk of hypothyroidism and in methods of treating a canine subject to reduce risk of hypothyroidism or to treat a canine subject that has hypothyroidism. The treatments comprise administering to the canine subject a low arginine diet and/or comprising an effective amount of a composition comprising a protein source, a carbohydrate source, a vegetable source, and a fruit source. Canine food compositions are disclosed.

8 Claims, 1 Drawing Sheet

Specification includes a Sequence Listing.

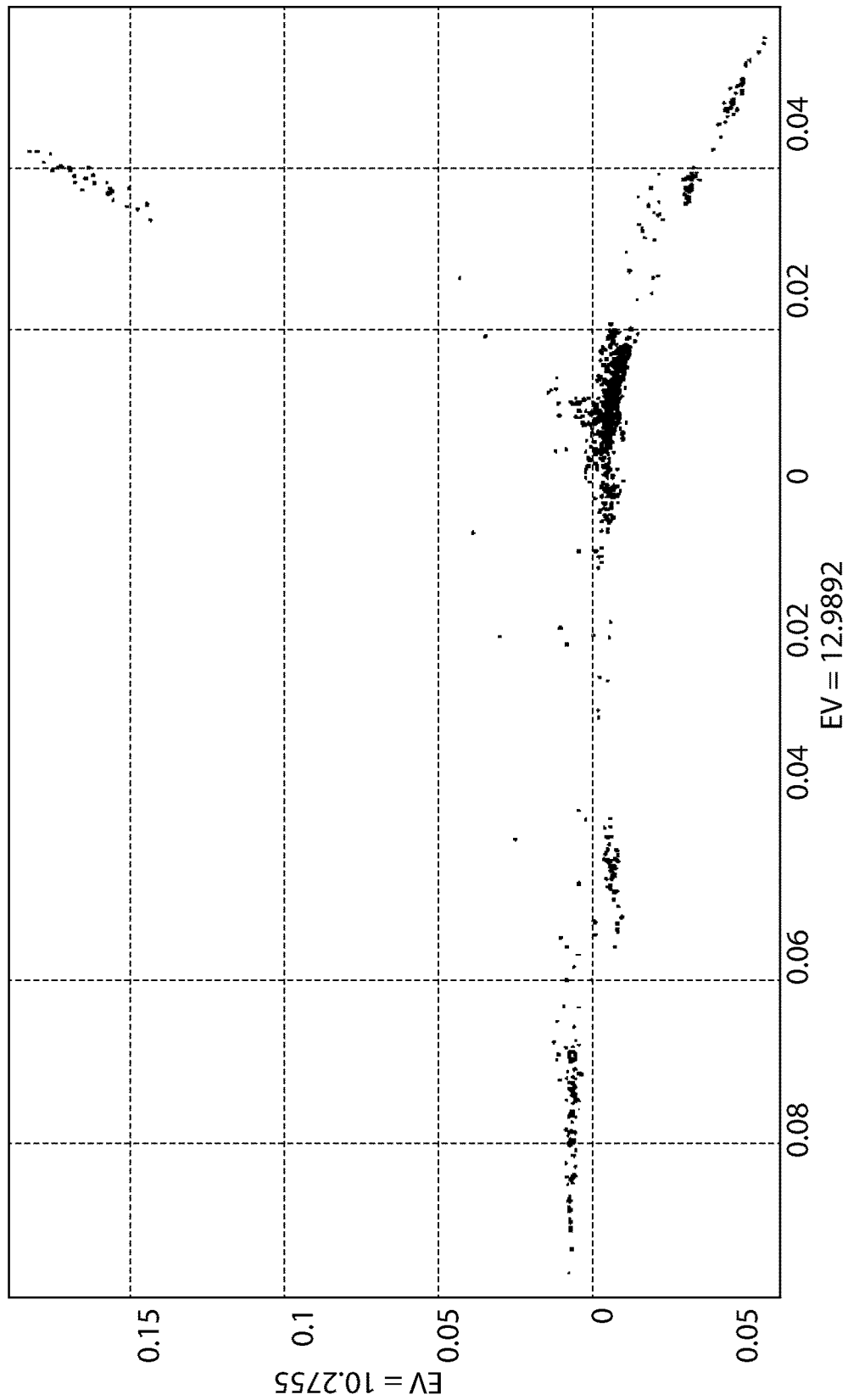

REAGENTS, KITS AND METHODS FOR ASSESSING AND REDUCING RISK OF DEVELOPING CANINE HYPOTHYROIDISM AND OTHER AUTOIMMUNE CONDITIONS

BACKGROUND

Canine hypothyroidism is the most common endocrine problem in dogs. The incidence estimates range from 1 in 156 to 1 in 500 animals. The onset of disease is typically in middle age (4-6 years). Canine hypothyroidism is the result of insufficient levels of thyroid hormone (T3/T4) and it treated with thyroid hormone supplementation (synthetic T4). While the prognosis for dogs that respond to therapy is good, the disease is a progressive. Dogs should be monitored regularly and the medication dose adjusted as needed.

Canine hypothyroidism is an autoimmune condition and antibodies against thyroid hormone and thyroglobulin are often found in the serum of affected dogs. There are two histological classifications of primary hypothyroidism, Lymphocytic thyroiditis (characterized by lymphocytic infiltration of the thyroid tissue) and idiopathic atrophy, which is thought to be the end stage to lymphocytic thyroiditis where the thyroid tissue has been mostly destroyed.

Not all dogs are at equal risk of developing hypothyroidism. There is a breed predisposition indicating that there is some heritable component to the disease.

Single nucleotide polymorphisms (SNPs) are a common type of genetic variation. SNPs are single base pair mutations at a specific locus. That is, a SNP is a difference in a single nucleotide in a DNA sequence that occurs at a specific position in a genome. Typically, for a SNP at a specific position, there are two possible nucleotide variations, which are referred to as alleles for that position. Within a population, the nucleotide variation that most commonly appears at a specific base position in a genome is referred to as the major allele; the nucleotide variation that is less common at that specific base position is referred to as the minor allele. Dogs, like most multicellular organisms have two sets of chromosomes. Thus, each dog has two copies of each gene or locus and therefore two copies of each SNP. Accordingly, for each SNP in the dog's genome, the dog may have two copies of the major allele, one minor allele and one minor allele or two minor alleles.

SNPs can act as biological markers. Some SNPs have been found helpful in predicting drug responses and risk of developing particular diseases. SNP genotyping refers to detection of SNPs within the genome. There are numerous methods for detecting SNPs and performing SNP genotyping.

There is a need to develop improved methods to identify dogs having increased likelihood or risk of developing hypothyroidism and other autoimmune conditions, for methods of reducing risk of canine hypothyroidism and other autoimmune conditions in such dogs, and for methods of preventing or delaying the onset of canine arthritis of the hip in dogs identified as having an increased likelihood of developing arthritis of the hip.

BRIEF SUMMARY

Methods that detecting the presence of either one or two copies of minor allele T of SNP Affx-206229307 and one or two copies of minor allele A of SNP Affx-206560187 in a sample obtained from a canine subject are provided. Methods of identifying a canine subject as having the TA haplotype for SNP Affx-206229307 and SNP Affx-206560187 are provided. The methods comprise analyzing a biological sample obtained from the canine subject for the presence of either one or two copies of minor allele T of SNP Affx-206229307; or one or two copies of minor allele A of SNP Affx-206560187; or one or two copies of minor allele T of SNP Affx-206229307 and one or two copies of minor allele A of SNP Affx-206560187. Either detecting the presence of one or two copies of minor allele T of SNP Affx-206229307, or detecting the presence of one or two copies of minor allele A of SNP Affx-206560187, or detecting the presence of one or two copies of minor allele T of SNP Affx-206229307 and one or two copies of minor allele A of SNP Affx-206560187 indicates that the canine subject has the TA haplotype for SNP Affx-206229307 and SNP Affx-206560187.

Methods of identifying a canine subject as having an increased likelihood of developing hypothyroidism are provided. The methods comprise the step of analyzing a biological sample obtained from the canine subject for the presence of either one or two copies of minor allele T of SNP Affx-206229307; or one or two copies of minor allele A of SNP Affx-206560187; or one or two copies of minor allele T of SNP Affx-206229307 and one or two copies of minor allele A of SNP Affx-206560187. The presence of one or two copies of minor allele T of SNP Affx-206229307; or one or two copies of minor allele A of SNP Affx-206560187; or one or two copies of minor allele T of SNP Affx-206229307 and one or two copies of minor allele A of SNP Affx-206560187 indicates that the canine subject has an increased likelihood of developing hypothyroidism.

In some embodiments, samples are analyzed by performing DNA sequencing, restriction enzyme digest, polymerase chain reaction (PCR), hybridization, real-time PCR, reverse transcriptase PCR, or ligase chain reaction. In some embodiments, the sample is a genomic DNA sample. In some embodiments, the sample is obtained from blood, saliva, follicle root, nasal swab or oral swab of the feline subject, preferably saliva. In some embodiments, the sample is analyzed by performing at least one nucleic acid analysis technique selected from: analysis using a whole genome SNP chip, single-stranded conformational polymorphism (SSCP) assay, restriction fragment length polymorphism (RFLP), automated fluorescent sequencing; clamped denaturing gel electrophoresis (CDGE); denaturing gradient gel electrophoresis (DGGE), mobility shift analysis, restriction enzyme analysis, heteroduplex analysis, chemical mismatch cleavage (CMC), RNase protection assays, use of polypeptides that recognize nucleotide mismatches, allele-specific PCR, sequence analysis, and SNP genotyping. In some embodiments, the sample is analyzed by performing at least one nucleic acid analysis technique selected from: hybridization-based methods, enzyme-based methods, post-amplification methods based on physical properties of DNA, and sequencing methods.

Method of reducing risk of hypothyroidism in a canine subject are provided. The methods comprise identifying the canine subject as being a canine subject with an increased likelihood of developing hypothyroidism and feeding the canine subject a daily diet of a low arginine nutritional composition and/or a diet of a comprising an effective amount of a composition comprising a protein source, a carbohydrate source, a vegetable source, and a fruit source; wherein the protein source is selected from the group consisting of chicken, egg protein, corn gluten meal, and combinations thereof; wherein the carbohydrate source is selected from the group consisting of millet, brewers rice, oat groats, and combinations thereof; wherein the vegetable source is selected from the group consisting of carrots, spinach, tomato pomace, and combinations thereof; and wherein the fruit source is citrus pulp.

Method of treating a canine that has hypothyroidism are provided. The methods comprise identifying the canine as having the TA haplotype for SNP Affx-206229307 and SNP Affx-206229307 and feeding the canine subject a daily diet of a low arginine nutritional composition and/or a diet of a comprising an effective amount of a composition comprising a protein source, a carbohydrate source, a vegetable source, and a fruit source; wherein the protein source is selected from the group consisting of chicken, egg protein, corn gluten meal, and combinations thereof wherein the carbohydrate source is selected from the group consisting of millet, brewers rice, oat groats, and combinations thereof; wherein the vegetable source is selected from the group consisting of carrots, spinach, tomato pomace, and combinations thereof and wherein the fruit source is citrus pulp.

Low arginine canine food composition that are also provided.

BRIEF DESCRIPTION OF THE DRAWINGS

FIG. 1 shows data described in Example 2 showing population structure.

DETAILED DESCRIPTION

The following description of the preferred embodiment(s) is merely exemplary in nature and is in no way intended to limit the invention, its application, or uses.

As used herein and in the appended claims, the singular forms "a", "an", and "the" include plural reference unless the context clearly dictates otherwise.

The term "dog" includes those dogs which are companion animals such as *Canis familiaris*, working dogs and the like. The term dog is synonymous with the term canine.

Compositions and methods are provided for treating a canine subject with an increased likelihood or risk of hypothyroidism to reduce the likelihood of hypothyroidism, to delay the onset of hypothyroidism and/or to reduce the severity of hypothyroidism. The treatment comprises feeding the canine subject a low arginine diet. The compositions and methods are useful to reduce the likelihood of hypothyroidism, to delay the onset of hypothyroidism and/or to reduce the severity of hypothyroidism treat a symptom of anxiety or stress in such animals that are in need thereof. In some embodiments, the canine subject has been identified as having an increased risk of developing hypothyroidism. In some embodiments, the canine subject is identified as having an increased risk of developing hypothyroidism by detecting the presence of genetic markers, in particular a specific haplotype for two SNPs, in the canine subject's genome. In some embodiments, the canine subject who has no symptoms. In some embodiments, the canine subject is exhibiting symptoms or otherwise suspected of having hypothyroidism. In some embodiments, the methods are treatment methods that comprise the steps of identifying the canine subject as having an increased risk of developing hypothyroidism, such as by detecting the presence of genetic markers, in particular a specific haplotype for two SNPs, in the canine subjects genome, and then feeding the canine subject a low arginine diet.

As used herein, the term "treatment" refers to eliminating, reducing the severity or preventing hypothyroidism or one or more symptoms of hypothyroidism. Treatment refers to therapeutic and/or prophylactic activity. In a canine with symptoms of hypothyroidism, treatment refers to eliminating symptoms, arresting or reducing progression of symptoms, reducing severity of symptoms and preventing symptoms. Treatment that initially eliminate, arrests, reduces progression of or reduces severity of symptoms may continue and the continuing treatment may further eliminate, arrests, reduces progression of or reduces severity of symptoms and/or prevent return or development of symptoms or reduce severity of further development of symptoms. In some embodiments, prior to treating the canine, the canine may be identified as having a higher risk of hypothyroidism by detecting the presence of genetic markers. In some embodiments, prior to treating the canine, the canine may be identified as having symptoms of hypothyroidism. In some embodiments, a canine may be treated for hypothyroidism without identifying symptoms of hypothyroidism prior to treatment. In some embodiments, prior to treatment for hypothyroidism, a canine may be identified as being predisposed to having or developing hypothyroidism.

Compositions are provided that can serve as a daily diet having low arginine content. The compositions useful in the methods may be a dog food composition.

Genetic association studies revealed genetic markers that can be used identify dogs as being at an increased likelihood or risk for developing hypothyroidism. The identity of the genetic factors linked to an increased risk for developing hypothyroidism provides insight into phenotypic differences and their effects in canines at elevated risk for developing hypothyroidism. Such insight allows for strategies to minimize the effects of the phenotypic differences by manipulating intake, processing, production and elimination of specific nutrients. In a dog identified as having the genetic markers which indicate an increased likelihood or risk for developing hypothyroidism, nutritional intervention can reduce the likelihood of developing hypothyroidism, delay the onset and/or slowing the progression of the disease.

After genotyping a cohort of dogs using a canine high-density genotype array containing genetic markers across the entire dog genome, a whole genome association study was undertaken on a group of dogs clinically diagnosed with hypothyroidism and a group of age-matched, control dogs. Two SNPs, Affx-206229307 and Affx-206560187, exceeded genome wide significance in a basic association test and survived permutation testing. Additional analysis using a logistic model with population structure as a covariant identified these same two SNPs exceeding genome wide significance.

The minor allele in SNP Affx-206229307 is T and the major allele is C. The minor allele in SNP Affx-206560187 is A and the major allele is G. The two SNPs are tightly linked, they are very close to each other in the genome and are inherited together. The variants occur together. The presence of a minor allele in SNP Affx-206229307 occurs together with the presence of the minor allele in SNP Affx-206560187.

Since the variants occur together, the two SNPs are referred to herein as a haplotype. Thus, the haplotype TA indicates the minor alleles at each SNP. Genotyping for either SNP allows for the genotype of the other SNP to be inferred. Detecting the presence of minor allele T in SNP Affx-206229307 allows one to infer the presence of minor allele A in SNP Affx-206560187, and therefore the haplotype TA. Likewise, detecting the presence of minor allele A in SNP Affx-206560187 allows one to infer the presence of minor allele T in SNP Affx-206229307, and therefore the haplotype TA.

SNP Affx-206560187 and SNP Affx-206229307 occur on chromosome 12. Dogs have 39 pairs of chromosomes including a pair of chromosome 12s. That is, a dog has two copies of chromosome 12. The TA haplotype may occur on both chromosomes of the chromosome 12 pair or only on one of the two copies of chromosome 12, the other copy thereby having a major allele-major allele haplotype for the SNPs. The presence of the TA haplotype on only one of the two copies of chromosome 12 may render the canine as being a dog with an increased likelihood or risk of developing hypothyroidism. Accordingly, the genome may be interrogated for the presence of one minor allele or for the presence of both minor alleles of the haplotype; the presence of a minor allele indicated the canine has at least one chromosome 12 with the TA haplotype. The presence of zero minor alleles indicates that dog does not have a TA haplotype on either copy of chromosome 12.

As described herein, increased likelihood or risk of developing hypothyroidism refers to having a greater than average chance that an individual dog will develop hypothyroidism compared to that of a population of dogs. The incidence of hypothyroidism among dogs that have the TA haplotype TA is greater than the incidence of hypothyroidism among dogs that do not have the TA haplotype TA. That is, hypothyroidism occurs in dogs that have the TA haplotype at a higher rate than it does in dogs that do not have the TA haplotype.

Methods are provided for identifying a canine subject with an increased likelihood or risk of hypothyroidism and for treating such canine subjects in order to reduce likelihood of hypothyroidism. The treatment methods comprise the step of feeding the canine subject a low arginine diet. In some embodiments, the methods for identifying a canine with an increased likelihood or risk of hypothyroidism and for treating such canine subjects in order to reduce risk of hypothyroidism comprise analyzing a sample from the canine subject to detect the presence of minor allele T for SNP Affx-206229307 and thereby to determine if the canine subject has a TT or TC genotype for SNP Affx-206229307, which also indicates that the canine subject has the AA or AG genotype, respectively, for SNP Affx-206560187. In some embodiments, the methods for identifying a canine with an increased likelihood or risk of hypothyroidism and for treating such canine subjects in order to reduce risk of hypothyroidism comprise analyzing a sample from the canine subject to detect the presence of minor allele A for SNP Affx-206560187 and thereby to determine if the canine subject has an AA or AG genotype for SNP Affx-206560187, which also indicates that the canine subject has the TT or TC genotype, respectively, for SNP Affx-206229307. In some embodiments, the methods for identifying a canine with an increased likelihood or risk of hypothyroidism and for treating such canine subjects in order to reduce risk of hypothyroidism comprise analyzing a sample from the canine subject to detect the presence of minor allele T for SNP Affx-206229307 and the presence of minor allele A for SNP Affx-206560187. The presence of minor allele T for SNP Affx-206229307 indicates the canine subject has a TT or TC genotype for SNP Affx-206229307; the presence of the minor allele A for SNP Affx-206560187 indicates that the canine subject has the AA or AG genotype for SNP Affx-206560187. Whether the presence of minor allele T for SNP Affx-206229307 is detected and from that the presence of the minor allele A for SNP Affx-206560187 is inferred, or the presence of the minor allele A for SNP Affx-206560187 is detected and the presence of minor allele T for SNP Affx-206229307 is inferred, or the presence of both the minor allele T for SNP Affx-206229307 and the minor allele A for SNP Affx-206560187 are detected, the canine is identified as having the TA haplotype.

As used herein, low arginine diet refers to a daily diet having a low level of arginine as expressed as a percent total daily nutritional intake based on percent of total dry weight (not calories). A low level of arginine corresponds to 1.84% or less of arginine as a percent of total daily nutritional intake based on percent of total dry weight. In some embodiments, low arginine diet refers to 1.04-1.84% arginine as a percent of total daily nutritional intake based on percent of total dry weight. In some embodiments, low arginine diet refers to a daily diet having 1.21% or less arginine as expressed as a percent total daily nutritional intake based on percent of total dry weight. In some embodiments, low arginine diet refers to a daily diet having 1.11% or less arginine as expressed as a percent total daily nutritional intake based on percent of total dry weight. In some embodiments, the compositions include food compositions contain less than 1.04% arginine based on the total weight of the composition on a dry matter basis. Table 14 below is an excerpt from Table 10 that appears in the reference text "Nutrient Requirements of Domestic Animals: Nutrient Requirements of cats, Revised Edition, National Academy Press Washington. DC. 1986. page 63-67" which lists the percentage of particular amino acids in various protein sources used in pet food compositions. The excerpted portion in Table 14 shows the % arginine. Those skilled in the art could readily formulate a suitable dog food to provide the daily nutritional requirements for a dog as disclosed in Official Publication of the Association of American Feed Control Officials, Inc. (AAFCO), Atlanta, Ga., (2012). Using the table in "Nutrient Requirements of Domestic Animals: Nutrient Requirements of cats, Revised Edition, National Academy Press Washington. DC. 1986. page 63-67" which is designated Table 10 in the reference and excerpted in relevant part in Table 14 herein, those skilled in the art could readily formulate a suitable dog food to provide the daily nutritional requirements while restricting the level of arginine to 1.84% or less of the total daily nutritional intake based on percent of total dry weight, and in some embodiments arginine at a level of arginine between 1.04-1.84% of the total daily nutritional intake based on percent of total dry weight, and in some embodiments arginine at a level of 1.21% or less of the total daily nutritional intake based on percent of total dry weight, and in some embodiments arginine at a level of 1.11% or less of the total daily nutritional intake based on percent of total dry weight "Daily nutritional intake" and "total nutritional intake per day" refers to dry matter intake per day. That is, water weight is not included in calculating the amount of nutrition consumed per day. To the extent that food and food ingredient contain water/moisture, the dry matter represents everything in the sample other than water including protein, fiber, fat, minerals, etc. Dry matter weight is the total weight minus the weight of any water. Dry matter intake per day is calculated as the total nutritional intake per day excluding all water. For example, an amount of an ingredient equal to a specific percent of daily nutritional intake refers to the amount of that ingredient in dry matter form (i.e. excluding all water) relative to the total amount of dry matter consumed (also excluding all water) in a day. The skilled artisan would readily recognize and understand nutritional amounts and percentages expressed as dry matter amounts, dry matter weights and dry matter percentages. Since foods, whether wet, moist or dry, generally contain as certain amount of water, when calculating daily dry matter intake, the water component of such food is excluded. To calculate total daily nutritional intake, which is dry matter intake per day, water is excluded. To calculate percent of an ingredient of total daily intake on a dry matter basis, water is removed from the total intake to give total daily dry matter intake and the percent of the ingredient is based on amount of ingredient present as dry matter. Reference to a low arginine a daily diet of a canine that is a low arginine diet that contains a specific % or less arginine per total daily nutritional intake or that contains less than a specific % arginine per total daily nutritional intake and reference to a low arginine nutritional composition that contains less than a specific % arginine per total daily nutritional intake or a specific % or less of arginine per total daily nutritional intake and similar recitals are meant to establish the limit or range of arginine consumed daily as a percentage of the total amount of food/nutrition fed/consumed daily. The amount of arginine consumed by/fed to the dog per day does not exceed the specific percentage recited. All amounts are based on a dry matter weight basis. For example, "a low arginine a daily diet of a canine that is a low arginine diet that contains 1.21% or less arginine per total daily nutritional intake" means that for every 100 grams of dry matter weight of total food/nutrition fed/consumed by a dog in/over the course of a single day, the dry matter weight of the arginine component of the 100 grams of dry matter weight of total food/nutrition is 1.21 grams or less.

A "food," "food composition," "pet food composition" or "cat food composition" can, in some embodiments, be a nutritionally complete diet for dog to which it is fed.

As used herein, an "ingredient" refers to any component of a composition.

The term "nutrient" refers to a substance that provides nourishment. In some cases, an ingredient may comprise more than one "nutrient," for example, a composition may comprise corn comprising important nutrients including both protein and carbohydrate.

Food compositions can be provided to in the form of dog food. A variety of commonly known types of dog foods are available to dog owners. The selection of dog food includes but is not limited to wet dog food, semi-moist dog food, dry dog food and dog treats. Wet dog food generally has a moisture content greater than about 65%. Semi-moist dog food typically has a moisture content between about 20% and about 65% and may include humectants, potassium sorbate, and other ingredients to prevent microbial growth (bacteria and mold). Dry dog food such as but not limited to food kibbles generally has a moisture content below about 15%. Pet treats typically may be semi-moist, chewable treats; dry treats in any number of forms, or baked, extruded or stamped treats; confection treats; or other kinds of treats as is known to one skilled in the art.

As used herein, the term "kibble" or "food kibble" refers to a particulate pellet like component of dog feeds. In some embodiments, a food kibble has a moisture, or water, content of less than 15% by weight. Food kibbles may range in texture from hard to soft. Food kibbles may range in internal structure from expanded to dense. Food kibbles may be formed by an extrusion process or a baking process. In non-limiting examples, a food kibble may have a uniform internal structure or a varied internal structure. For example, a food kibble may include a core and a coating to form a coated kibble. It should be understood that when the term "kibble" or "food kibble" is used, it can refer to an uncoated kibble or a coated kibble.

As used herein, the term "extrude" or "extrusion" refers to the process of sending preconditioned and/or prepared ingredient mixtures through an extruder. In some embodiments of extrusion, food kibbles are formed by an extrusion processes wherein a kibble dough, including a mixture of wet and dry ingredients, can be extruded under heat and pressure to form the food kibble. Any type of extruder can be used, examples of which include but are not limited to single screw extruders and twin-screw extruders. The list of sources, ingredients, and components as described hereinafter are listed such that combinations and mixtures thereof are also contemplated and within the scope herein.

As contemplated herein, compositions are meant to encompass, but not be limited to, nutritionally-complete and balanced dog food compositions. A "nutritionally complete diet" is a diet that includes sufficient nutrients for maintenance of normal health of a healthy dog on the diet. Nutritionally complete and balanced dog food compositions are familiar to one of skill in the art. For example, substances such as nutrients and ingredients suitable for nutritionally complete and balanced animal feed compositions, and recommended amounts thereof, may be found for example, in the Official Publication of the Association of American Feed Control Officials, Inc. (AAFCO), Atlanta, Ga., (2012).

Genetic Factors Indicating Increased Likelihood of Canine Hypothyroidism

Table 1 provides information regarding each of SNPs Affx-206229307 and Affx-206560187. As noted in the table, both SNPs map to canine chromosome 12. SNP Affx-206229307 maps to chromosome 12 position 252750. SNP Affx-206560187 maps to chromosome 12 position 254127. The minor and major alleles for Affx-206229307 are T and C, respectively. The minor and major alleles for SNP Affx-206560187 are A and G, respectively. The most significant haplotype corresponds to the combination of minor alleles, and thus is TA.

TABLE 1

| Marker | Chromosome | Position | Minor/Major Allele |
| --- | --- | --- | --- |
| Affx-206229307 | 12 | 252750 | T/C |
| Affx-206560187 | 12 | 254127 | A/G |

Each SNP occurs at a locus that lies within the ARG1 gene, which is located in the dog major histocompatibility complex genome region. The ARG1 gene encodes the enzyme arginase 1 (referred to herein as arginase). The allele of ARG1 that has the TA haplotype is a significant risk factor for the development of hypothyroidism and possibly other autoimmune disorders in dogs.

Nitric oxide (NO) regulates immune activity; it is a pro-immune molecule (with respect to normal immunity and autoimmunity) and ARG1 is an important regulator of NO in immune function. In this way, ARG1 has a regulatory effect on immune activity.

Increased NO (production/levels/activity) corresponds to increased immune activity, while decreased NO corresponds to decreased immune activity. When released, NO is cytotoxic to invading pathogens, induces immune cell recruitment to sites of infection and is a regulator of Th1/Th2 T cell balance in a normal immune response. NO has also been implicated in autoimmune disease-causing host tissue destruction, immune infiltrate, enhanced cytotoxic T cell activity.

NO is produced by a reaction from arginine. More specifically, the inducible nitric oxide synthase (iNOS) converts arginine into NO and a reaction by-product, citrulline, which is itself a starting material in a series of reactions called the citrulline-NO pathway that produces and replenish arginine.

The arginine produced by the citrulline-NO pathway is converted by iNOS into NO and citrulline.

Arginase, which hydrolyzes arginine to ornithine and urea, provides a mechanism to down-regulate the production of NO in the nitric oxide response. In macrophages, arginase competes with iNOS for free arginine. The activity of arginase in which arginine is hydrolyzed to ornithine and urea, effectively decreases the amount of arginine available to act as a substrate for iNOS to produce NO and citrulline. By competing for arginine, the activity of arginase to process arginine limits NO production by reducing the amount of NO produced from arginine by iNOS and by reducing the amount of citrulline produced from arginine by iNOS that would be used in the citrulline-NO pathway to make more arginine.

Accordingly, arginase, the protein product of the ARG1 gene, regulates NO production and thereby regulates normal immune responses and autoimmune responses. The level of expression of the ARG1 gene, the amount of arginase protein produced, and the stability and level of activity of arginase effects NO production. An increase in expression of the ARG1 gene and/or an increase arginase production and/or activity reduces NO production, which in turn down-regulates normal immune responses and autoimmune response, while a decrease in expression of the ARG1 gene and/or a decrease in arginase production and/or activity results in an increase of NO production and increases normal immune responses and autoimmune response.

Without intending to be bound to any theory, the two SNP haplotype TA represents an allele that encodes a variant of ARG1 that may either have decreased expression and/or produce an arginase with decreased arginase activity, resulting in a diminished ability to convert arginine to ornithine and urea, thus decreasing the negative regulation of NO. That is, the minor alleles of these polymorphism may result in a reduction in arginase and/or an arginase with reduced activity. By having reduced expression or activity, dogs with the ARG1 minor allele genotypes do not have an arginase that competes with iNOS for arginine as effectively compared to dogs with the ARG1 major allele genotype. Thus, more NO is produced in dogs with the ARG1 minor allele genotypes resulting in increased immune responses. The resulting over-production of NO is a contributing factor to autoimmunity and the development of hyperthyroidism in dogs.

A significant reduction in circulating arginine concentration and a significant reduction in circulating citrulline concentration can be achieved by feeding dogs a low arginine diet. The low arginine diet reduces risk for developing hypothyroidism.

The treatment used to reduce the likelihood or risk of developing hypothyroidism in a canine subject identified as having a higher likelihood or risk of developing hypothyroidism comprises feeding the canine subject a low arginine diet. Methods of treating dogs to reduce the likelihood of developing hypothyroidism are provided that comprise identifying a canine subject as a dog having a higher likelihood or risk of developing hypothyroidism and feeding the dog a low arginine diet. In some embodiments, the low arginine diet is also a high fiber diet. In some embodiments, treatment methods comprise the steps of: 1) identifying a dog as having higher likelihood or risk of developing hypothyroidism by performing a genotypic analysis to identify the canine as having the TA haplotype and feeding the cat a low arginine diet.

Kits, reagents, other articles, and compositions useful in methods for identifying a canine subject as being a dog with a higher likelihood or risk of developing hypothyroidism are provided. The kits, reagents, other articles, and compositions may be useful in methods that evaluate genotype in order to detect the TA haplotype. Kits, reagents, other articles, and compositions useful methods are provided for treating canine subjects to prevent, reduce the likelihood, delay the onset, and/or reduce the severity of hypothyroidism. The canine subjects may be identified as having an increased likelihood of developing hypothyroidism by methods provided herein. The methods of treating canine subjects to prevent, reduce the likelihood, delay the onset, and/or reduce the severity of hypothyroidism may comprises feeding the canine subjects a low arginine diet.

Affx-206229307 and Affx-206560187

Affx-206229307

Affx-206229307 refers to the SNP located at canine chromosome 12, position 252750 in the CanFam3.1 reference genome (chr12:252750). Affx-206229307 is located at a locus within the canine ARG1 gene.

SEQ ID NO:1—Affx-206229307 SNP is shown in a 200 nucleotide sequence located at nucleotide 101 plus 100 bp upstream and 99 bp downstream.

```
>canFam3_dna range = chr12:252650-252849 5'pad =
100 3'pad = 100 strand = + repeatMasking = none
5'-TCAAATTCCC ATTCTTGGCA ACAAGCACCC ACCACCCCTC

TGCCTGACAC ATTCTGCTCT CTTCCTTCGT TCCCTTCTTG

CATGACCGCC CCACACACCG [T/C]CTTCATTGA GCAGATATAA

TTGCCCCTTC TTTAAACCTC AATCCAGGGA CCCCTGGGTG

GTTCAGTGGT GAGTGTCTGC CTTTGGCTCA GGGTGTAATC-3'
```

Affx-206560187

Affx-206560187 refers to the SNP located at canine chromosome 12, position 254127 in the CanFam3.1 reference genome (chr12:254127). Affx-206560187 is located at a locus within the canine ARG1 gene.

SEQ ID NO:2-Affx-206560187 SNP is shown in a 201 nucleotide sequence located at nucleotide 101 plus 100 bp upstream and 100 bp downstream.

```
>canFam3_dna range = chr12:254027-254227 5'pad =
100 3'pad = 100 strand = + repeatMasking = none
5'-CCACCTTTTC TTCCTTTTGT TCAGTTATTT TAATTCTGTC

TTCATCAAAG CCCATCCCAA GAATAAGGGA GTATATTGCA

GTTTTGCGAT TAACGCGAGC [A/G]CTAGAAGAA ACACTTCTAT

GTCAGCAAAA TGTCCCCGTG TTCTGGGAGA GAACT TTGAA

GGAGG ACGGG GGAAGTGCAG CAGTGTTTAC TGACA GTCCA

G-3'
```

Genomic sequences containing the disclosed SNPs can be accessed in a number of ways. The chromosome and location defined by the Dog reference genome CanFam3.1 for the SNP Affx-206229307 is chr12:252750. The chromosome and location defined by the Dog reference genome CanFam3.1 for the SNP Affx-206560187 is chr12:254127. Those skilled in the art can use a publicly available interface such as the University of California Santa Cruz Genome browser to locate the SNP of interest and extract the flanking DNA sequences using genome browser tools. Furthermore, the dog reference Genome is publicly available from numerous sources such as <ftp://ftp.ensembl.org/pub/release-94/fasta/canis_familiaris/dna/> or <http://hgdownload.cse.ucsc.edu/goldenPath/canFam3/bigZipsi> or <ftp://ftp.ncbi.nlm.nih.gov/genomes/all/GCA/000/002/285/GCA_000002285.2_CanFam3.1>. These databases can be used to extract the relevant DNA sequences.

Methods of detecting single nucleic acid polymorphisms associated with an increased risk for developing hypothyroidism in a canine subject are provided. Methods of identifying dogs with the TA haplotype which is associated with an increased likelihood of hypothyroidism in a canine subject are provided. Methods of identifying dogs at increased risk for developing hypothyroidism are provided. Methods of reducing the risk for developing hypothyroidism in a canine are provided. Methods reducing the risk for developing hypothyroidism in a canine may result in prevention of hypothyroidism, the reduction of symptoms, the reduction in the severity of symptoms or the delay in the onset of symptoms. Methods reducing the risk for developing hypothyroidism in a canine identified as being at an increased or elevated risk of developing hypothyroidism are provided. Kits, reagents and composition used to detect the TA haplotype, determine risk of developing hypothyroidism, identify dogs at increased risk of developing hypothyroidism and reducing the likelihood of developing hypothyroidism and treating dogs are provided.

The canine subject may be interrogated for the presence a TA haplotype by detecting at least one minor allele at either SNP. In some embodiments, canine subject may be interrogated for the presence one minor allele of the TA haplotype or both minor alleles of the TA haplotype. Detection of the TA haplotype based upon interrogation of an individual canine's genome can be used to identify a canine subject as having a higher likelihood or risk of developing hypothyroidism.

In some embodiments, a sample from the canine subject can be interrogated for the presence of both the minor allele T and the minor allele to detect the presence of the TA haplotype. In some embodiments, a sample from the canine subject can be interrogated for the presence of either one of the minor allele T and the minor allele to detect the presence of the TA haplotype. The absence of detection of the minor alleles indicates that the canine is homozygous for the major allele/major allele CG haplotype.

In some embodiments, a sample from the canine subject can be interrogated for the presence of the major allele C of Affx-206229307 and/or the major allele G of Affx-206560187 to detect the presence of the CG haplotype. While a sample must be interrogated for minor allele T of Affx-206229307 and/or the minor allele A of Affx-206560187 to detect the presence of the TA haplotype, if the sample is interrogated for the presence of the major allele C of Affx-206229307 and/or the major allele G of Affx-206560187 to detect the presence of the CG haplotype and no major allele is detected, i.e. the CG haplotype is not present, the subject thereby has the TA haplotype on each copy of chromosome 12 and may thereby be at a higher risk and/or a risk for more severe hypothyroidism.

In some embodiments, the sample is a genomic DNA sample. In some embodiments, the sample is obtained from blood, saliva, follicle root, nasal swab or oral swab of the canine subject. In some embodiments, the biological sample is a genomic DNA sample from the canine subject using the commercially available kit such as PERFORMAgene PG-100 Oral sample collection it (DNA Genotek, OraSure Technologies, Inc., Bethlehem, Pa.).

In some embodiments, methods comprise identifying dogs with the TA haplotype. That is, the methods comprise either: detecting the presence one or two copies of the minor allele T of SNP Affx-206229307 located at chr12:252750; or detecting the presence one or two copies of the minor allele A of SNP Affx-206560187 located at chr12:254027-254227; or detecting the presence one or two copies of the minor allele T of SNP Affx-206229307 located at chr12:252750 and detecting the presence one or two copies of the minor allele A of SNP Affx-206560187 located at chr12:254027-254227.

In some embodiments, the TA haplotype is detected using methods that include at least one nucleic acid analysis technique selected from: DNA sequencing, restriction enzyme digest, polymerase chain reaction (PCR), hybridization, real-time PCR, reverse transcriptase PCR, or ligase chain reaction.

In some embodiments, the TA haplotype is detected by performing at least one nucleic acid analysis technique selected from the group consisting of: analysis using a whole genome SNP chip; single-stranded conformational polymorphism (SSCP) assay; restriction fragment length polymorphism (RFLP); automated fluorescent sequencing; clamped denaturing gel electrophoresis (CDGE); denaturing gradient gel electrophoresis (DGGE); mobility shift analysis; restriction enzyme analysis; heteroduplex analysis; chemical mismatch cleavage (CMC); RNase protection assays; use of polypeptides that recognize nucleotide mismatches; allele-specific PCR; sequence analysis; and SNP genotyping.

In some embodiments, the TA haplotype is detected using a method selected from the types of methods consisting of: hybridization-based methods, enzyme-based methods, post-amplification methods based on physical properties of DNA, and sequencing methods.

In some embodiments, the TA haplotype is detected using a method selected from the types of methods consisting of: hybridization-based methods selected from the group consisting of: dynamic allele-specific hybridization, molecular beacon methods and SNP microarrays; enzyme-based methods selected from the group consisting of: restriction fragment length polymorphism (RFLP), PCR-based methods, Flap endonuclease, primer extension methods, 5'-nuclease and oligonucleotide ligation assay; post-amplification methods based on physical properties of DNA selected from the group consisting of: single strand conformation polymorphism, temperature gradient gel electrophoresis, denaturing high performance liquid chromatography, high-resolution amplicon melting, DNA mismatch-binding proteins, SNPlex, and surveyor nuclease assay; and sequencing methods In some embodiment, the TA haplotype is detected using a high-density array that contains genetic markers including the genetic markers for interrogating one or both SNPs.

In some embodiment, the TA haplotype is detected using a low-density array that contains genetic markers for interrogating one or both SNPs.

In some embodiment, the TA haplotype is detected using a high-density array containing genetic markers. Examples of arrays include the commercially available microarrays such as the GeneChip® Canine Genome 2.0 Array (Affymetrix, Thermo Fisher Scientific, Waltham, Mass.), Dog Genome Microarray (Core Life Sciences, Irvine Calif.), the Illumina Canine HD panel and an additional 50,000-100,000 custom genetic markers (SNPs) (The Illumina Canine HD panel and an additional 50,000-100,000 custom genetic markers (SNPs) such as Infinium® iSelect® Custom Genotyping Assays (Illumina, Inc. San Diego, Calif.).

In some embodiments, the MassARRAY System is used in the detection of the presence of the TA haplotype. The MassARRAY System is a non-fluorescent detection platform utilizing mass spectrometry to accurately measure PCR-derived amplicons. Mass spectrometry, coupled with end point PCR, enables highly multiplexed reactions under universal cycling conditions to provide accurate, rapid, and cost-effective analysis. The MassARRAY System offers a unique solution for targeted genetic testing with limited input material.

In some embodiments, bead array technology is used in the detection of the TA haplotype. For example, technology such as that included in the Illumina BeadArray technology and the Infinium HD assay (Illumina, Inc. San Diego, Calif.) may be used. In some embodiments, bead array technology is used in the detection of the presence of SNP alleles. The Illumina BeadArray technology is based on small silica beads that self-assemble in microwells on planar silica slides. Each bead is covered with hundreds of thousands of copies of a specific oligonucleotide that act as a capture sequence in the Infinium assay. Once the beads have self-assembled, a proprietary decoding process maps the location of every bead, ensuring that each one is individually quality controlled. The result of this manufacturing process is that every BeadChip undergoes rigorous testing to assure the highest possible quality standards. The Infinium assay can be scaled to unlimited multiplexing without compromising data quality, unlike many alternative PCR-dependent assays. The simple streamlined workflow is common across all products, no matter how many SNPs are being interrogated. Likewise, the data acquisition process and analysis are the same. The Infinium assay protocol features single-tube sample preparation and whole genome amplification without PCR or ligation steps significantly reducing labor and sample handling errors. After hybridizing unlabeled DNA sample on the BeadChip, two-step allele detection provides high call rates and accuracy. Selectivity and specificity are accomplished in two-steps. Target hybridization to bead-bound 50-mer oligos provides high selectivity while enzymatical single-base extension also incorporates a labeled nucleotide for assay readout. The staining reagent is optimized to provide a higher signal, and more balanced intensities between red and green channels. These features contribute to accuracy, high call rates and copy number data with low noise. The Infinium assay produces two-color readouts (one color for each allele) for each SNP in a genotyping study. Intensity values for each two-color channels, A and B, convey information about the allelic ratio at a single genomic locus. Typical studies incorporate values for a large number of samples (hundreds to tens of thousands) to ensure significant statistical representation. When these values are appropriately normalized and plotted distinct patterns (or clusters) emerge, in which samples have identical genotypes at an assayed locus exhibit similar signal profiles (A and B values) and aggregate in clusters. For diploid organisms, bi-allelic loci are expected to exhibit three clusters (AA, AB and BB). Genotype calls are based upon information derived from standard cluster file, which provides statistical data from a representative sample set. This enables genotypes to be called by referencing assay single intensities against known data for a given locus. Since the call accuracy is tied to the quality of the cluster data, having efficient and robust clustering algorithm is essential for accurate genotyping. The Illumina Gebtrain2 algorithm accurately and efficiently identifies cluster patters of genotyping samples and reports summary.

SNP alleles may be detected using hybridization-based methods. Examples of hybridization-based methods include dynamic allele-specific hybridization, methods that employ molecular beacons, and methods that employ SNP microarrays including high-density oligonucleotide SNP arrays or low-density oligonucleotide SNP arrays. SNPs can be interrogated by hybridizing complementary DNA probes to the SNP site. In dynamic allele-specific hybridization, a genomic segment is amplified and attached to a bead through a PCR reaction with a biotinylated primer. The amplified product is then attached to a streptavidin column and washed to remove the unbiotinylated strand. An allele-specific oligonucleotide is then added in the presence of a molecule that fluoresces when bound to double-stranded DNA. The intensity is measured as temperature is increased until the melting temperature (Tm) can be determined. SNP are detected by their lower than expected Tm. Specifically engineered single-stranded oligonucleotide probes are used in SNP detection that uses molecular beacons. Oligonucleotides are designed in which complementary regions are at each end and a probe sequence is located in between such that probe take on a hairpin, or stem-loop, structure in its natural, isolated state. A fluorophore is attached to one end of the probe a fluorescence quencher is attached to the other end. The fluorophore is in close proximity to the quencher when the oligo is in a hairpin configuration and the molecule does not emit fluorescence. The probe sequence is complementary to the genomic DNA used in the assay. If the probe sequence of the molecular beacon encounters its target genomic DNA during the assay, it will anneal and hybridize. The oligo will no longer assume the hairpin configuration and will fluoresce. High-density oligonucleotide SNP arrays comprise hundreds of thousands of probes arrayed on a small chip, allowing for many SNPs to be interrogated simultaneously. Several redundant probes designed to have the SNP site in several different locations as well as containing mismatches to the SNP allele are used to interrogate each SNP. The differential amount of hybridization of the target DNA to each of these redundant probes, allows for specific homozygous and heterozygous alleles to be determined.

The TA haplotype may be detected using enzyme-based methods. A broad range of enzymes including DNA ligase, DNA polymerase and nucleases may be employed. Examples of enzyme-based methods include methods based upon restriction fragment length polymorphism (RFLP), PCR-based methods, methods that utilize Flap endonuclease; methods that utilize primer extension, methods that utilize 5'-nuclease and methods that include oligonucleotide ligation assays. RFLP methods to detect SNPs use many different restriction endonucleases to digestion a genomic sample. It is possible to ascertain whether or not the enzymes cut the expected restriction sites by determining fragment lengths through a gel assay. RFLP assays are designed to include enzymes that cut in the presence or absence of SNPs and the pattern of fragment lengths can be used to determine the presence or absence of SNPs. PCR based methods include tetra-primer amplification refractory mutation system PCR, or ARMS-PCR, and multiple qPCR reactions. Tetra-primer amplification refractory mutation system PCR, or ARMS-PCR, employs two pairs of primers to amplify two alleles in one PCR reaction. The primers are designed such that the two primer pairs overlap at a SNP location but each match perfectly to only one of the possible SNPs. Alternatively, multiple qPCR reactions can be run with different primer sets that target each allele separately. Some embodiments utilize Flap endonuclease (FEN), which is an endonuclease that catalyzes structure-specific cleavage. This cleavage is highly sensitive to mismatches and can be used to interrogate SNPs with a high degree of specificity. A FEN called cleavase is combined with two specific oligonucleotide probes, that together with the target DNA, can form a tripartite structure recognized by cleavase. The first probe, called the Invader oligonucleotide is complementary to the 3' end of the target DNA. The last base of the Invader oligonucleotide is a non-matching base that overlaps the SNP nucleotide in the target DNA. The second probe is an allele-specific probe which is complementary to the 5' end of the target DNA, but also extends past the 3' side of the SNP nucleotide. The allele-specific probe will contain a base complementary to the SNP nucleotide.

Primer extension is a two-step process that first involves the hybridization of a probe to the bases immediately upstream of the SNP nucleotide followed by a 'mini-sequencing' reaction, in which DNA polymerase extends the hybridized primer by adding a base that is complementary to the SNP nucleotide. This incorporated base is detected and determines the SNP allele. The primer extension method is used in a number of assay formats. These formats use a wide range of detection techniques that include MALDI-TOF Mass spectrometry (see Sequenom) and ELISA-like methods. Sequenom's iPLEX SNP genotyping method, which uses a MassARRAY mass spectrometer. The flexibility and specificity of primer extension make it amenable to high throughput analysis. Primer extension probes can be arrayed on slides allowing for many SNPs to be genotyped at once. Referred to as arrayed primer extension (APEX), this technology has several benefits over methods based on differential hybridization of probes.

Illumina Incorporated's Infinium assay is an example of a whole-genome genotyping pipeline that is based on primer extension method. In the Infinium assay, over 100,000 SNPs can be genotyped. The assay uses hapten-labelled nucleotides in a primer extension reaction. The hapten label is recognized by antibodies, which in turn are coupled to a detectable signal. APEX-2 is an arrayed primer extension genotyping method which is able to identify hundreds of SNPs or mutations in parallel using efficient homogeneous multiplex PCR (up to 640-plex) and four-color single-base extension on a microarray. The multiplex PCR requires two oligonucleotides per SNP/mutation generating amplicons that contain the tested base pair. Methods that utilize 5'-nuclease include methods using Taq DNA polymerase's 5'-nuclease activity in the TaqMan assay for SNP genotyping. The TaqMan assay is performed concurrently with a PCR reaction and the results can be read in real-time as the PCR reaction proceeds. In methods that include oligonucleotide ligation assays, oligonucleotide DNA ligase catalyzes the ligation of the 3' end of a DNA fragment to the 5' end of a directly adjacent DNA fragment. This mechanism can be used to interrogate a SNP by hybridizing two probes directly over the SNP polymorphic site, whereby ligation can occur if the probes are identical to the target DNA. Examples of other post-amplification methods for detecting SNPs include methods based upon DNA's physical properties. Such methods first involve PCR amplification of the target DNA.

Several methods of detecting SNP alleles are based upon DNA's physical properties such as melting temperature and single stranded conformation. Methods that use single stranded conformation are based upon single-stranded DNA (ssDNA) that folds into a tertiary structure. The conformation is sequence dependent and most single base pair mutations will alter the shape of the structure. When applied to a gel, the tertiary shape will determine the mobility of the ssDNA, providing a mechanism to differentiate between SNP alleles. This method first involves PCR amplification of the target DNA. The double-stranded PCR products are denatured using heat and formaldehyde to produce ssDNA. The ssDNA is applied to a non-denaturing electrophoresis gel and allowed to fold into a tertiary structure. Differences in DNA sequence will alter the tertiary conformation and be detected as a difference in the ssDNA strand mobility. Temperature gradient gel electrophoresis (TGGE) or temperature gradient capillary electrophoresis (TGCE) methods are based on the principle that partially denatured DNA is more restricted and travels slower in a gel or other porous material. In another method, denaturing high performance liquid chromatography (DHPLC) uses reversed-phase HPLC to interrogate SNPs. In DHPLC, the solid phase which has differential affinity for single and double-stranded DNA. Another method used is high-resolution melting of the entire amplicon. Use of DNA mismatch-binding proteins may also be used to detect SNPs. MutS protein from Thermus aquaticus binds different single nucleotide mismatches with different affinities and can be used in capillary electrophoresis to differentiate all six sets of mismatches. SNPlex is a proprietary genotyping platform sold by Applied Biosystems. Surveyor nuclease assay uses surveyor nuclease, a mismatch endonuclease enzyme that recognizes all base substitutions and small insertions/deletions (indels), and cleaves the 3' side of mismatched sites in both DNA strands. Sequencing technologies can also be used in SNP detection. Advances in sequencing technology allow SNP detection by sequencing more practical.

Genotyping by sequencing using next generation sequencing technologies has become a common practice. Genotyping by sequencing, also called GBS, is a method to discover single nucleotide polymorphisms (SNP) in order to perform genotyping studies, such as genome-wide association studies (GWAS). GBS uses restriction enzymes to reduce genome complexity and genotype multiple DNA samples. After digestion, PCR is performed to increase fragments pool and then GBS libraries are sequenced using next generation sequencing technologies. With the advancement of next generation sequencing technologies such as Illumina short read sequencing by synthesis and PacBio's single molecule real time sequencing it is becoming more feasible to do GBS. In the future, development of new technologies such as nanopore single molecule sequencing may allow whole genome sequencing/genotyping.

Compositions and Formulations

Application of the methodology outlined above has identified bioactive dietary components that have been combined to provide compositions, foods, and diets that provide significant benefits to dogs identified that will benefit from a treatment to reduce the likelihood of canine hypothyroidism. The risk of canine hypothyroidism in canine subjects with the TA haplotype can be significantly reduced by feeding a low arginine diet.

The food product is a nutritionally complete diet for an adult canine. In a specific aspect, the food product is a nutritionally complete diet formulated for an adult companion canine.

In some embodiments, the compositions include food compositions contain less than 1.84% or less of arginine based on the total weight of the composition on a dry matter basis. In some embodiments, the compositions include food compositions contain 1.04-1.84% arginine based on the total weight of the composition on a dry matter basis. In some embodiments, the compositions include food compositions contain 1.21% or less of arginine based on the total weight of the composition on a dry matter basis. In some embodiments, the compositions include food compositions contain 1.11% or less of arginine based on the total weight of the composition on a dry matter basis. In some embodiments, the compositions include food compositions contain less than 1.04% arginine based on the total weight of the composition on a dry matter basis. The compositions may comprise protein in an amount from 4% to 75% or more based on the total weight of the composition on a dry matter basis, fat in an amount from 5% to 50% or more based on the total weight of the composition on a dry matter basis, and carbohydrate from 5% to 75% or more based on the total weight of the composition on a dry matter basis, wherein the food composition is suitable for consumption by a dog.

In some embodiments, such compositions are nutritionally complete and balanced low arginine compositions which contain, in some embodiments 1.04-1.84%, in some embodiments 1.21% or less, and in some embodiments 1.11% or less of arginine. In some such embodiments, a nutritionally complete and balanced dog food composition may comprise: from 4% to 90%, from 5% to 75%, from 10% to 60% protein, and from 15% to 50% by weight of protein; from 0% to 90%, from 2% to 80%, from 5% to 75%, and from 10% to 50% by weight of carbohydrate; from 2% to 60%, from 5% to 50%, and from 10% to 35% by weight of fat. The compositions may further contain from 0 to 15% or from 2% to 8%, by weight of vitamins and minerals, antioxidants, and other nutrients which support the nutritional needs of the animal.

Sources of proteins, carbohydrates, fats, vitamins, minerals, balancing agents, and the like, suitable for inclusion in the compositions, and particularly in the food products to be administered in methods provided herein, may be selected from among those conventional materials known to those of ordinary skill in the art.

In some embodiments, proteins useful as ingredients of the food compositions may comprise proteins from animal sources, such as animal proteins, including mammalian, avian protein, reptilian, amphibian, fish, invertebrate proteins and combinations thereof; e.g., from any of cattle, sheep, pig, goat, deer, rabbit, horse, kangaroo, their milk, curds, whey or blood, and internal tissues and organs such as smooth muscle, striate muscle, liver, kidney, intestine or heart; additional avian protein sources encompass turkey, goose, duck, ostrich, quail, pigeon, their eggs and internal tissues and organs such as smooth muscle, striate muscle, liver, kidney, intestine or heart; amphibian sources include frog or salamander, reptilian protein sources include alligator, lizard, turtle and snake; a fish protein sources include catfish, herring, salmon, tuna, bluefish, cod, halibut, trout, swordfish and their eggs; and an invertebrate protein sources include lobster, crab, clams, mussels or oysters, and combinations thereof, meat protein isolate, whey protein isolate, egg protein, mixtures thereof, and the like, as well as vegetable sources, such as soy protein isolate, corn gluten meal, wheat gluten, mixtures thereof, and the like.

In some embodiments, carbohydrates useful as ingredients of the food compositions may include but are not limited to, one or more of corn, whole yellow corn, grain sorghum, wheat, barley, rice, millet, brewers rice, oat groats, and polysaccharides (e.g., starches and dextrins) and sugars (e.g., sucrose, lactose, maltose, glucose, and fructose) that are metabolized for energy when hydrolyzed. Examples of additional carbohydrate sources suitable for inclusion in the compositions disclosed herein include, fruits and non-tomato pomace vegetables.

Fats useful as ingredients of the food compositions may be from any source, such as but not limited to poultry fat, beef tallow, lard, choice white grease, soybean oil, corn oil, canola oil, sunflower oil, mixtures thereof, and the like. The fat may be incorporated completely within the food composition, deposited on the outside of the food composition, or a mixture of the two methods.

In some embodiments, the compositions further include an effective amount of one or more substances selected from the group consisting of glucosamine, chondroitin, chondroitin sulfate, methylsulfonylmethane ("MSM"), creatine, antioxidants, Perna canaliculata, omega-3 fatty acids, omega-6 fatty acids and mixtures thereof.

In some embodiments, the food composition further comprises one or more amino acid such as but not limited to arginine, histidine, isoleucine, leucine, lysine, methionine (including DL-methionine, and L-methionine), phenylalanine, threonine, tryptophan, valine, taurine, carnitine, alanine, aspartate, cystine, glutamate, glutamine, glycine, proline, serine, tyrosine, and hydroxyproline.

In some embodiments, the food composition further comprises one or more fatty acids such as but not limited to lauric acid, myristic acid, palmitic acid, palmitoleic acid, margaric acid, margaroleic acid, stearic acid, oleic acid, linoleic acid, g-linolenic acid, a-linolenic acid, stearidonic acid, arachidic acid, gadoleic acid, DHGLA, arachidonic acid, eicossatetra acid, EPA, behenic acid, erucic acid, docosatetra acid, and DPA.

In some embodiments, the food composition further comprises one or more macro nutrients such as but not limited to moisture, protein, fat, crude fiber, ash, dietary fiber, soluble fiber, insoluble fiber, raffinose, and stachyose.

In some embodiments, the food composition further comprises one or more micro nutrients such as but not limited to beta-carotene, alpha-lipoic acid, glucosamine, chondroitin sulfate, lycopene, lutein, and quercetin.

In some embodiments, the food composition further comprises one or more minerals such as but not limited to calcium, phosphorus, potassium, sodium, chloride, iron, copper, copper, manganese, zinc, iodine, selenium, selenium, cobalt, sulfur, fluorine, chromium, boron, and oxalate.

In some embodiments, the food composition further comprises one or more other vitamins, such as but not limited to vitamin A, vitamin C, vitamin D, vitamin E, quinoa grain, thiamine, riboflavin, niacin, pyridoxine, pantothenic acid, folic acid, vitamin B12, biotin, and choline.

In some embodiments, the food composition further comprises fiber, which may be supplied from a variety of sources, including, for example, vegetable fiber sources such as cellulose, beet pulp, peanut hulls, and soy fiber.

In some embodiments, the food composition further comprises stabilizing substances, for example, substances that tend to increase the shelf life of the composition. Potentially suitable examples of such substances include, for example, preservatives, antioxidants, synergists and sequestrants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches.

In some embodiments, the food composition further comprises additives for coloring, palatability, and nutritional purposes include, for example, colorants; iron oxide, sodium chloride, potassium citrate, potassium chloride, and other edible salts; vitamins; minerals; and flavoring. The amount of such additives in a composition typically is up to 5% (dry basis of the composition).

In some embodiments, compositions, foods, and diets that are useful to reduce the likelihood of and/or treat hypothyroidism in dogs comprise three protein sources (chicken, egg protein, and corn gluten meal), three carbohydrate sources (millet, brewers rice, and oat groats) as well as specific vegetables (carrots, spinach, and tomato pomace) and specific fruit ingredients (citrus pulp). In some embodiments, such compositions are nutritionally complete and balanced low arginine compositions which contain, in some embodiments 1.04-1.84%, in some embodiments 1.21% or less, and in some embodiments 1.11% or less of arginine.

In some embodiments, compositions, foods, and diets that are useful to reduce the likelihood of and/or treat hypothyroidism in dogs comprise a protein source, a carbohydrate source, a vegetable source, a fruit source, or a combination of two or more thereof. The protein source is selected from the group consisting of chicken, egg protein, corn gluten meal, and combinations thereof, while the carbohydrate source is selected from the group consisting of millet, brewers rice, oat groats, and combinations thereof. The vegetable source is selected from the group consisting of carrots, spinach, tomato pomace, and combinations thereof, and the fruit source is citrus pulp. In some embodiments, such compositions are nutritionally complete and balanced low arginine compositions which contain, in some embodiments 1.04-1.84%, in some embodiments 1.21% or less, and in some embodiments 1.11% or less of arginine.

In some embodiments, compositions, foods, and diets comprise chicken in an amount from 5% to 25% based on the total weight of the composition on a dry matter basis, and may optionally be low arginine compositions which contain, in some embodiments 1.04-1.84%, in some embodiments 1.21% or less, and in some embodiments 1.11% or less of arginine.

In some embodiments, compositions, foods, and diets comprise egg protein in an amount from 4% to 15% based on the total weight of the composition on a dry matter basis, and may optionally be low arginine compositions which contain, in some embodiments 1.04-1.84%, in some embodiments 1.21% or less, and in some embodiments 1.11% or less of arginine.

In some embodiments, compositions, foods, and diets comprise corn gluten meal in an amount from 6% to 20% based on the total weight of the composition on a dry matter basis, and may optionally be low arginine compositions which contain, in some embodiments 1.04-1.84%, in some embodiments 1.21% or less, and in some embodiments 1.11% or less of arginine.

In some embodiments, compositions, foods, and diets comprise carrots, spinach, tomato pomace, and combinations thereof, in an amount from 0.5% to 2% based on the total weight of the composition on a dry matter basis, and may optionally be low arginine compositions which contain, in some embodiments 1.04-1.84%, in some embodiments 1.21% or less, and in some embodiments 1.11% or less of arginine.

In some embodiments, compositions, foods, and diets comprise citrus pulp in an amount from 0.5% to 2% based on the total weight of the composition on a dry matter basis, and may optionally be low arginine compositions which contain, in some embodiments 1.04-1.84%, in some embodiments 1.21% or less, and in some embodiments 1.11% or less of arginine.

In certain embodiments, compositions comprise chicken in an amount of 5%, 7.5%, 10%, 12.5%, 15%, 17.5%, 20%, 22.5% or 25% based on the total weight of the composition on a dry matter basis, and may optionally be low arginine compositions which contain, in some embodiments 1.04-1.84%, in some embodiments 1.21% or less, and in some embodiments 1.11% or less of arginine. In particular aspects of these embodiments, compositions may comprise a dry weight of chicken within a range defined by any two of these values as endpoints.

In certain embodiments, compositions comprise egg protein in an amount of 4%, 5%, 6%, 7%, 8%, 9%, 10%, 11%, 12%, 13%, 14% or 15% based on the total weight of the composition on a dry matter basis, and may optionally be low arginine compositions which contain, in some embodiments 1.04-1.84%, in some embodiments 1.21% or less, and in some embodiments 1.11% or less of arginine. In particular aspects of these embodiments, compositions may comprise a dry weight of egg protein within a range defined by any two of these values as endpoints.

In certain embodiments, compositions comprise corn gluten meal in an amount of 6%, 7%, 8%, 9%, 10%, 11%, 12%, 13%, 14%, 15%, 16%, 17%, 18%, 19%, or 20% based on the total weight of the composition on a dry matter basis, and may optionally be low arginine compositions which contain, in some embodiments 1.04-1.84%, in some embodiments 1.21% or less, and in some embodiments 1.11% or less of arginine. In particular aspects of these embodiments, composition may comprise a dry weight of corn gluten meal within a range defined by any two of these values as endpoints In certain embodiments, compositions comprise a vegetable source in an amount of 0.5%, 0.6%, 0.7%, 0.8%, 0.9%, 1.0%, 1.1%, 1.2%, 1.3%, 1.4%, 1.5%, 1.6%, 1.7%, 1.8%, or 1.9%, or 2.0% based on the total weight of the composition on a dry matter basis, and may optionally be low arginine compositions which contain, in some embodiments 1.04-1.84%, in some embodiments 1.21% or less, and in some embodiments 1.11% or less of arginine. In particular aspects of these embodiments, composition may comprise a dry weight of a vegetable source within a range defined by any two of these values as endpoints.

In certain embodiments, compositions comprise a fruit source in an amount of 0.5%, 0.6%, 0.7%, 0.8%, 0.9%, 1.0%, 1.1%, 1.2%, 1.3%, 1.4%, 1.5%, 1.6%, 1.7%, 1.8%, or 1.9%, or 2.0% based on the total weight of the composition on a dry matter basis, and may optionally be low arginine compositions which contain, in some embodiments 1.04-1.84%, in some embodiments 1.21% or less, and in some embodiments 1.11% or less of arginine. In particular aspects of these embodiments, composition may comprise a dry weight of a citrus pulp within a range defined by any two of these values as endpoints.

In certain embodiments, compositions comprise a carbohydrate selected from millet, brewers rice, oat groats, and combinations thereof in an amount of 5%, 10%, 15%, 20%, 25%, 30%, 35%, 40%, 45%, or 50% based on the total weight of the composition on a dry matter basis, and may optionally be low arginine compositions which contain, in some embodiments 1.04-1.84%, in some embodiments 1.21% or less, and in some embodiments 1.11% or less of arginine. In particular aspects of these embodiments, composition may comprise a dry weight of a carbohydrate source within a range defined by any two of these values as endpoints.

In another aspect of this embodiment, the food comprises from 5% to 50% carbohydrate, by dry weight of the composition, selected from millet, brewers rice, oat groats, and combinations thereof, and may optionally be low arginine compositions which contain, in some embodiments 1.04-

1.84%, in some embodiments 1.21% or less, and in some embodiments 1.11% or less of arginine.

Preparation of Compositions

The low arginine compositions may be prepared as food products suitable for consumption by dogs. These food products may be of any consistency or moisture content; i.e., the compositions may be moist, semi-moist, or dry food products. "Moist" food products are generally those with a moisture content of from 60% to 90% or greater. "Dry" food products are generally those with a moisture content of from 3% to 11%, and are often manufactured in the form of small pieces or kibbles. "Semi-moist food products generally have a moisture content of from 25% to 35%. The food products may also include components of more than one consistency, for example, soft, chewy meat-like particles or pieces as well as kibble having an outer cereal component or coating and an inner "cream" component.

The low arginine food products may be prepared in a canned or wet form using conventional food preparation processes known to those of ordinary skill in the art. Typically, ground animal proteinaceous tissues are mixed with the other ingredients, such as cereal grains, suitable carbohydrate sources, fats, oils, and balancing ingredients, including special purpose additives such as vitamin and mineral mixtures, inorganic salts, cellulose, beet pulp and the like, and water in an amount sufficient for processing. The ingredients are mixed in a vessel suitable for heating while blending the components. Heating the mixture is carried out using any suitable manner, for example, direct steam injection or using a vessel fitted with a heat exchanger. Following addition of all of the ingredients of the formulation, the mixture is heated to a temperature of from 50° F. to 212° F. Although temperatures outside this range can be used, they may be commercially-impractical without the use of other processing aids. When heated to the appropriate temperature, the material will typically be in the form of thick liquid, which is dispensed into cans. A lid is applied and the container is hermetically sealed. The sealed can is then placed in convention equipment designed for sterilization of the contents. Sterilization is usually accomplished by heating to temperatures of greater than 230° C. for an appropriate time depending on the temperature used, the nature of the composition, and related factors. The compositions and food products of the present invention can also be added to or combined with food compositions before, during, or after their preparation.

In some embodiments, the food products may be prepared in a dry form using convention processes known to those of ordinary skill in the art. Typically, dry ingredients, including dried animal protein, plant protein, grains and the like are ground and mixed together. Liquid or moist ingredients, including fats, oils water, animal protein, water, and the like are added combined with the dry materials. The specific formulation, order of addition, combination, and methods and equipment used to combine the various ingredients can be selected from those known in the art. For example, in certain embodiments, the resulting mixture is process into kibbles or similar dry pieces, which are formed using an extrusion process in which the mixture of dry and wet ingredients is subjected to mechanical work at high pressure and temperature, forced through small openings or apertures, and cut off into the kibbles, e.g., with a rotating knife. The resulting kibble can be dried and optionally coated with one or more topical coatings comprising, e.g., flavors, fats, oils, powdered ingredients, and the like. Kibbles may also be prepared from dough by baking, rather than extrusion, in which the dough is placed into a mold before dry-heat processing.

In preparing a composition, any ingredient generally may be incorporated into the composition during the processing of the formulation, e.g., during and/or after mixing of the other components of the composition. Distribution of these components into the composition can be accomplished by conventional means. In certain embodiments, ground animal and/or poultry proteinaceous tissues are mixed with other ingredients, including nutritional balancing agents, inorganic salts, and may further include cellulose, beet pulp, bulking agents and the like, along with sufficient water for processing.

In some embodiments, the compositions are formulated so as to be easier to chew. In specific embodiments, the compositions and food products are formulated to address specific nutritional differences between dogs such as life stage, age, size, weight, body composition, and breed.

The low arginine compositions are formulated as a nutritionally complete diet to meet the needs of a mature adult feline. These nutritionally complete diets that include sufficient nutrients for maintenance of normal health of a healthy dog on the diet. Nutritionally complete and balanced dog food compositions are familiar to one of skill in the art. For example, substances such as nutrients and ingredients suitable for nutritionally complete and balanced animal feed compositions, and recommended amounts thereof, may be found for example, in the Official Publication of the Association of American Feed Control Officials, Inc. (AAFCO), Atlanta, Ga. (2012).

Compositions, when administered to reduce that risk for developing hypothyroidism comprise providing a dog that has been identified as being at-risk for developing hypothyroidism result in biological effects that may result in specific improvement in the levels of proteins associated with oxidation (peroxiredoxins), mineral transport (ceruloplasmin) and the immune system (proteasome).

All publications mentioned herein are incorporated by reference for the purpose of describing and disclosing the materials and methodologies that are reported in the publication, which might be used in connection with the invention.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

EXAMPLES

Example 1

A cohort of ~900 dogs were genotyped using the Affymetrix Canine High Density Genotype Array containing approximately 750,000 genetic markers across the entire dog genome. A whole genome association study was run on 125 dogs clinically diagnosed with hypothyroidism and 732 age matched controls. Two SNPs, Affx-206229307 and Affx-206560187, exceeded genome wide significance in a basic association test and survived permutation testing using a maximum of 5000 permutations. Additional analysis using a logistic model with population structure as a covariant identified these same two SNPs exceeding genome wide significance.

Example 2

Dog Cohort

The subjects in the study were a subset of a 1000 dog cohort. The subjects were client owned animals identified by approximately 20 veterinarian clinics across the United States. Inclusion criteria included being greater than 7 years of age and being of purebred status. No specific breeds were selected for. The cohort consisted of over 100 different dog breeds roughly representative of the breed demographics across the United States.

DNA Extraction

DNA samples were collected from 82 cases and 300 controls using the DNAGenotek saliva collection Kit. The collection sponge was placed inside the dog's mouth in the pocket between the cheek and gum for 30 seconds to absorb saliva and cells them placed in the stabilizing lysis solution and stored at −80° C. until DNA extraction. DNA was extracted by thawing the lysis solution and using a Qiagen DNA extraction kit as per manufacturer's directions.

Genotyping

Genome wide genotyping was performed using the Affymetrix Axiom Canine HD genotype array consisting of approximately 730,000 SNPs. Genotyping was filtered using Plink (https://www.cog-genomics.org/plink2) for minor allele frequency greater than 5 percent (—maf 0.05), dropping individuals missing more than 10% of genotyping calls (—mind 0.1), and dropping genotypes missing more than 10% of calls (—geno 0.1). 157,498 SNPs were removed by filtering leaving 571,678, SNPs for downstream analysis.

Phenotyping

Animals in the cohort were thoroughly examined by a qualified veterinarian. Based on client interviews and clinical examination dogs with any clinical signs of hypothyroidism were identified and diagnosed as such.

GWAS

As a first pass, a basic association test was run between the genotyped alleles and individuals affected with hypothyroidism. The analysis included a permutation test for each SNP in the analysis as a further layer of significance. (plink—dog—bfile dup_Affy_HD—pheno affy_hd_covariant.txt—1—pheno-name Hypothyroidism—assoc—mperm 5000—allow-no-sex—maf 0.05—out Hypothyroid_mperm). Only two SNPs passed both genome wide significance and the permutation testing.

SNPs Affx-206229307 and Affx-206560187 are in linkage disequilibrium ($r2=0.99$ $D'=1$) with the phased haplotypes of TA/CG. The odds ratio for the TA haplotype is greater than 3 and based on frequencies of the minor allele in the affected and unaffected populations, a risk ratio of 2.63.

A second genome wide association analysis was done use a logistic regression model with the first two eigen vectors from a PCA analysis of the cohort to take population structure into account. All genotypes were pruned for SNPs in LD ($r^2>0.5$) and Principal component analysis run using the SVS software from Golden Helix, Bolder Colo. The first two eigen vectors are plotted in FIG. 1 to show the population structure. (plink—dog—bfile dup_Affy_HD—pheno affy_hd_covariant.txt—1—pheno-name Hypothyroidism—logistic—allow-no-sex—covar affy_hd_covariant.txt—covar-number 1,2—maf 0.05—out ~/JeffWork/Affy_genotypes/Targets/Hypo_log_covar). Using this model, the two SNPs in the ARG1 gene remain significant (Table 2) although just below genome wide significance.

TABLE 2

| CHR | SNP | BP | A1 | F_A | F_U | A2 | CHISQ | P | OR |
|---|---|---|---|---|---|---|---|---|---|
| 12 | Affx-206229307 | 252750 | T | 0.212 | 0.0806 | C | 41.05 | 1.48E−10 | 3.069 |
| 12 | Affx-206560187 | 254127 | A | 0.212 | 0.08208 | G | 39.67 | 3.01E−10 | 3.069 |

CHR Chromosome
SNP SNP ID
BP Chromosomal location
A1 Minor Allele
F_A Frequency in Affected
F_U Frequency in Unaffected
A2 Major Allele
CHISQ Chi Square Value
P pValue
OR Odds Ratio

TABLE 3

| CHR | SNP | EMP1 | EMP2 |
|---|---|---|---|
| 12 | Affx-206229307 | 0.0002 | 0.0224 |
| 12 | Affx-206560187 | 0.0002 | 0.03519 |

CHR Chromosome
SNP SNP ID
EMP1 Permutation pValue
EMP2 Adjusted pValue

TABLE 4

| CHR | SNP | BP | A1 | TEST | NMISS | OR | STAT | P |
|---|---|---|---|---|---|---|---|---|
| 12 | Affx-206229307 | 252750 | T | ADD | 857 | 2.338 | 5.201 | 1.99E−10 |
| 12 | Affx-206560187 | 254127 | A | ADD | 0.856 | 2.311 | 5.134 | 2.83E−10 |

CHR Chromosome
SNP SNP ID
BP Chromosomal location
A1 Minor Allele
TEST Additive allele model
OR Odds Ratio based on the Regression slope
P pValue

Example 3

In a study conducted to evaluate the ability of food to change circulating arginine and ornithine concentrations, healthy adult dogs were fed increased arginine food (1.11 vs 1.21 percent). The lower arginine food resulted in a significant reduction in circulating arginine concentration (0.66 of the higher food) and a significant reduction in circulating citrulline concentration (0.34 if the higher arginine food). The data shows that food below 1.21 percent arginine, preferably 1.11 or below, is effective to significantly reduce both circulating arginine concentration and circulating citrulline concentration.

Example 4

A saliva sample is obtained from a canine. The sample may be shipped as collected to a laboratory at another location, partially processed and then shipped to a laboratory at another location or completely processed and analyzed at a laboratory and the site of collection. If the sample is shipped as collected to a laboratory at another location or partially processed and then shipped to a laboratory at another location, results which may include some or all data collected from the sample by the laboratory may be transmitted to the site of collection and/or a veterinarian and/or the owner of or responsible party for the canine. After the saliva sample is obtained, it may be processed for analysis and evaluated for the presence of 1 or 2 copies of the minor allele of Affx-206229307 and/or 1 or 2 copies of the minor allele of Affx-206560187. Dogs having the presence of 1 or 2 copies of the minor allele of Affx-206229307 and/or 1 or 2 copies of the minor allele of Affx-206560187 are considered as having a higher likelihood of developing hypothyroidism.

Example 5

Samples are collected from canines using PERFORMAgene PG-100 Oral collection kit.

When doing so, the animal should not eat for 30 minutes or drink for 10 minutes before saliva collection, the individual doing the collection should not scrape the animal's teeth or cheek with the sponge nor should the animal be allowed to chew or bite the sponge.

The collection tube provided as part of the PERFORMAgene PG-100 Oral collection kit contains liquid that preserves the DNA sample and is required by the lab to analyze the sample. The cap should not be removed prior to sample collection.

In the first step of the collection protocol, the sponge is placed in the animal's mouth at the cheek pouch. Saliva is collected for 30 seconds by moving sponge and mopping saliva where it naturally pools (in the cheek pouch and under the tongue). For animals older than 6 months, moderate restraint may be required.

Next, holding the tube upright, the cap from the tube is unscrewed. The cap is turned upside down and the oral swab is placed in the tube. The cap is screwed on tightly to prevent liquid sample from leaking during transport. The tube is inverted and shaken vigorously numerous times, e.g. 10 times, to thoroughly mix sample.

A permanent marker may be used to clearly write the animal identification number on the white space available on the tube label.

The step-by-step laboratory protocol for manual purification of DNA from 0.5 mL aliquot of a Performagene™ sample that has been collected and preserved in Performagene chemistry with the PG-100 collection kit is as follows. The Reagents required for manual purification are available with PG-AC1 reagent package or PG-AC4 reagent package.

When a DNA sample is collected and mixed with the Performagene solution, the DNA is immediately stabilized Performagene samples are stable at room temperature for 1 year from the time of collection. Performagene samples can be stored indefinitely at −15° C. to −20° C., and can undergo multiple freeze-thaw cycles without deterioration of the DNA.

The following equipment and reagents are used in the purification process: a Microcentrifuge capable of running at 15,000×g; an air or water incubator at 50° C.; ethanol (95% to 100%) at room temperature; DNA buffer: TE (10 mM Tris-HCl, 1 mM EDTA, pH 8.0) or similar solution; optional glycogen (20 mg/mL) (e.g., Invitrogen Cat. No. 10814-010); ethanol (70%) at room temperature and 5M NaCl solution.

In the first step, the sample is mixed by shaking vigorously for 5 seconds. This is to ensure that viscous samples are properly mixed with the Performagene solution.

The sample is incubated in a 50° C. air incubator for a minimum of 2 hours, or in a 50° C. water incubator for a minimum of 1 hour. DNA in Performagene is stable at room temperature even without the incubation step. This heat-treatment step is essential to ensure that DNA is adequately released and that nucleases are permanently inactivated. This incubation step may be performed at any time after sample is collected from the animal and before it is purified. Incubation of the entire sample is recommended. The sample may be incubated at 50° C. overnight if it is more convenient. A longer time is required in an air incubator because temperature equilibration is slower than in a water incubator.

Optionally, the collection sponge may be removed. The cap is removed and the collection sponge is pressed against the inside of the tube to extract as much of the sample as possible. The sponge and cap are discarded. Sponge removal is dictated by preference of workflow.

Next, 500 µL of the mixed Performagene sample is transferred to a 1.5 mL microcentrifuge tube. The remainder of the Performagene sample can be stored at room temperature or frozen (−15° C. to −20° C.). 20 µL (1/25th volume) of PG-L2P purifier is then added to the microcentrifuge tube and mix ed by vortexing for a few seconds. The sample becomes turbid as impurities and inhibitors are precipitated.

The sample is incubated on ice for 10 minutes (room temperature incubation can be substituted but will be slightly less effective in removing impurities) followed by centrifugation at room temperature for 5 minutes at 15,000× g. A longer period of centrifugation (up to 15 minutes) may be beneficial in reducing the turbidity (high A320) of the final DNA solution. The clear supernatant is transferred with a pipette tip into a fresh microcentrifuge tube and the pellet, which contains turbid impurities, is discarded. To 500 µL of supernatant, 25 µL (1/20$^{th}$ volume) of 5 M NaCl is added followed by mixing. The addition of NaCl is necessary to ensure efficient recovery of DNA. To 500 µL of supernatant, 600 µL of room temperature 95% to 100% ethanol is added followed by gentle mixing by inversion 10 times. During mixing with ethanol, the DNA will be precipitated. The DNA may appear as a clot of DNA fibers or as a fine precipitate, depending upon the amount of DNA in the sample. Even if no clot is seen, DNA will be recovered by carefully following the next steps.

The sample is allowed to stand at room temperature for 10 minutes to allow the DNA to fully precipitate. The tube is then placed in the centrifuge in a known orientation (DNA pellet may not be visible after centrifugation) and centrifuged at room temperature for 2 minutes at >15,000×g. For example, each tube may be placed in the microcentrifuge with the hinge portion of the cap pointing away from the center of the rotor. After centrifugation, the position of the pellet can be located (even if too small to be easily visible); it will be at the tip of the tube below the hinge.

The supernatant is removed with a pipette tip and discarded. The pellet contains DNA. Rotating the tube such that the pellet is on the upper wall will allow you to safely move a pipette tip along the lower wall and remove all of the supernatant. The supernatant may contain impurities and should be removed as completely as possible. Excessive drying of the pellet can make the DNA more difficult to dissolve. The DNA is washed by first adding 250 μL of 70% ethanol, then letting it stand for 1 minute at room temperature. The ethanol is removed with a pipette tip without disturbing the pellet. The 70% ethanol wash helps to remove residual inhibitors. Complete removal of ethanol, however, is essential to prevent inhibition during downstream applications. Therefore, the tube is centrifuged for 6 seconds to pool any remaining ethanol, which is removed with a pipette tip.

100 μL of DNA buffer (e.g. TE buffer) is added to the tube to dissolve the DNA pellet. Vortexing for at least 5 seconds aids in the dissolving process. To ensure complete rehydration of the DNA, let sit at room temperature overnight. DNA can now be quantified and used in downstream applications.

Assays that use fluorescent dyes are more specific than absorbance at 260 nm for quantifying the amount of double-stranded DNA (dsDNA) in a DNA sample. To quantify the DNA by fluorescence method, fluorescent dyes such as PicoGreen® or SYBR® Green I may be used to quantify dsDNA since there is less interference by contaminating RNA. Alternatively, commercially available kits such as Invitrogen's Quant-iT™ PicoGreen dsDNA Assay Kit (Cat. No. Q-33130) can be used. For either protocol, the purified DNA is preferably diluted 1:50 with TE solution and 5 μL is used in the quantification assay.

Alternatively, DNA may be quantified by absorbance in which case the purified sample is preferable first treated with RNase to digest contaminating RNA and then remove the RNA fragments by ethanol precipitation of the DNA. DNA from a Performagene sample typically contains appreciably more RNA than found in blood samples. Ensure that alcohol-precipitated DNA is fully dissolved before reading the absorbance. An absorbance of 1.0 at 260 nm corresponds to a concentration of 50 ng/μL (50 μg/mL) for pure dsDNA. A spectrophotometer cuvette capable of reading a volume of 100 μL or less should be used to avoid using too large a volume of sample. Absorbance values at 260 nm should be between 0.1 and 1.5. Lower values may not be reliable.

A 10 μL aliquot of purified RNase-treated DNA is diluted with 90 μL of TE (1/10 dilution) and mixed by gently pipetting up and down. Wait for bubbles to clear. TE is used in the reference (blank) cell. The absorbance is measured at 320 nm, 280 nm and 260 nm. Corrected $A_{280}$ and $A_{260}$ values are calculated by subtracting the absorbance at 320 nm ($A_{320}$) from $A_{280}$ and $A_{260}$ values. DNA concentration in ng/μL=corrected $A_{260}$×10 (dilution factor)×50 (conversion factor). $A_{260}/A_{280}$ ratio: divide corrected $A_{260}$ by corrected $A_{280}$.

Example 6

Pre-Feed, Control Food, and Test Food (Food Compositions to reduce risk of hypothyroidism in a dog that has been identified as being at-risk for developing hypothyroidism)

The foods administered to the canines include a Pre-feed composition provided to the animals before initiation of the studies, as well as a Control Food and an illustrative Test Food to reduce risk of hypothyroidism in a dog that has been identified as being at-risk for developing hypothyroidism. The levels of moisture, ash, protein, crude fat, fiber, and total fatty acids in these foods are provided in Table 5, below.

TABLE 5

| Ingredient | Pre-Feed | Control Food | Test Food |
| --- | --- | --- | --- |
| Moisture | 9.3% | 8.0% | 7.1% |
| Ash | 4.6% | 4.8% | 4.2% |
| Crude Fat | 8.9% | 15.3% | 14.0% |
| Crude Fiber | 1.5% | 3.6% | 1.0% |
| Crude Protein | 20.1% | 19.3% | 18.0% |
| Total Fatty Acids | 7.5% | 14.1% | 12.0% |
| Carbohydrate* | 55.6% | 49.1% | 55.7% |

*Carbohydrate (Nitrogen-free extract) = 100% − (% Protein + % Fat % Ash + % Fiber + % Moisture)

The Test Food is formulated with protein sources that included chicken, egg protein, and corn gluten meal, carbohydrate sources including millet, brewers rice, and oat groats, and vegetable sources including carrots, spinach, and tomato pomace, as well as citrus pulp. Although similar in overall composition, the Control Food may not necessarily include the combination of chicken, egg protein, corn gluten meal, millet, brewers rice, oat groats, carrots, spinach, tomato pomace, and citrus pulp, much less each within the concentrations described herein. That is, although the Control and Test Foods are both formulated to meet the nutritional requirements of the canines to be fed those compositions, the sources of ingredients used to formulate those diets differ from one another.

Example 7

Improvement in Resistance to Oxidative Stress

Feeding dogs the Test Food set forth in Table 5 improves levels of three specific proteins, peroxiredoxin-1, ceruloplasmin, and proteasome-1, each of which is associated with amelioration of oxidative stress. The levels of each of ceruloplasmin, peroxiredoxins-1, and proteasome rise markedly as compared to base-line data as well as the data obtained with dogs provided the Control Food. Since each of these enzymes is involved in the body's defenses to oxidative stress, administration of the Test Food may be useful to reduce risk of hypothyroidism in a dog that has been identified as being at-risk for developing hypothyroidism. Determination of the levels of each may be carried out using standard laboratory reagents, assays, and protocols.

Example 8

Table 6 describes certain embodiments having proportion of the composition (% of dry weight of component composition) that includes total arginine present at 1.84% or less, and in some embodiments, total arginine present at 1.21% or less, and in some embodiments, total arginine present at 1.11% or less, and in some embodiments, total arginine present at less than 1.04%, and in some embodiments, total arginine present at 1.04-1.84%.

TABLE 6

| Protein | from about 5% to about 70%, or from about 10% to about 70%, or from about 10% to about 60% |
| --- | --- |

TABLE 6-continued

| | |
|---|---|
| Carbohydrate (preferably a nitrogen-free or essentially nitrogen-free extract) | from about 0% to about 50%, or from about 5% to about 45% |
| Fat | from about 2% to about 50%, or from about 5% to about 50%, or from about 5% to about 40% |
| Dietary fiber | from about 0% to about 40%, or from about 1% to about 20%, or from about 1% to about 5.5% |
| Nutritional balancing agents (e.g., vitamins, and minerals) | from about 0% to about 15%, or from about 2% to about 8% |

Example 9

Table 7 describes certain embodiments having proportion of the composition (% of dry weight of component composition) that includes total arginine present at 1.84% or less, and in some embodiments, total arginine present at 1.21% or less, and in some embodiments, total arginine present at 1.11% or less, and in some embodiments, total arginine present at less than 1.04%, and in some embodiments, total arginine present at 1.04-1.84%.

TABLE 7

| Description | Content Range (w/w %) |
|---|---|
| Chicken, livers, hydrolyzed, dry | 25-45 |
| Hyvital ® wheat glutamine PN | 0.25-2 |
| Lysine, 1, hydrochloride | 0.1-0.75 |
| Methionine, dl | <0.08 |
| Taurine | 0.075-0.2 |
| Captex ® 355 Medium Chained Triglyceride | 1-5 |
| Cellulose, coarse | 1-5 |
| Beet, pulp | 1-3 |
| OatWell ® 22 oat bran | 2-5 |
| Pecan Fiber | 1-5 |
| MEG-3 ® 0355TG Fish Oil | 0.5-2.5 |
| Ginger Root Powder | 0.5-2 |
| Cranberry Pomace | 0.1-0.4 |
| Pomegranate Extract WS | 0.1-0.4 |
| Green Tea PE 50% EGCG WS | 0.1-0.4 |
| Boswellia PE 65% Boswellic Acids | 0.05-0.3 |
| Sensimune ™ 75 (Yeast Cell Wall) | 0.05-0.3 |

Example 10

Table 8 describes certain embodiments having proportion of the composition (% of dry weight of component composition) that includes total arginine present at 1.84% or less, and in some embodiments, total arginine present at 1.21% or less, and in some embodiments, total arginine present at 1.11% or less, and in some embodiments, total arginine present at less than 1.04%, and in some embodiments, total arginine present at 1.04-1.84%.

TABLE 8

| Ingredient | w/w % |
|---|---|
| Chicken, livers, hydrolyzed, dry | 36.79 |
| Corn, starch, common canning | 32.45 |
| Choice White Grease | 1.00 |
| Mineral, premix, 2305 | 0.08 |
| Vitamin E, oil, 29% | 0.10 |
| Hyvital ® Wheat Glutamine PN | 1.00 |
| Lysine, 1, hydrochloride | 0.50 |
| Methionine, dl | 0.07 |
| Taurine | 0.10 |
| Captex ® 355 Medium Chained Triglyceride | 4.00 |

TABLE 8-continued

| Ingredient | w/w % |
|---|---|
| Cellulose, coarse | 3.00 |
| Lactic acid, food grade | 1.50 |
| Dicalcium phosphate | 1.20 |
| Chicken, liver, digest, optimizor LDPE H | 2.00 |
| Sodium chloride, iodized | 0.40 |
| Choline chloride, liquid, 70% | 0.25 |
| Calcium carbonate | 2.00 |
| Potassium chloride | 0.70 |
| Beet, pulp | 2.50 |
| OatWell ® 22 oat bran | 3.00 |
| Pecan Fiber | 2.00 |
| MEG-3 ® 0355TG Fish Oil | 1.50 |
| Ginger Root Powder | 1.00 |
| Palatant | 0.75 |
| Natural flavor, Pork, Liver, Digest, D'T | 0.50 |
| Glyceryl monostearate | 0.25 |
| Cranberry Pomace | 0.20 |
| Pomegranate Extract WS | 0.20 |
| Green Tea PE 50% EGCG WS | 0.20 |
| Boswellia PE 65% Boswellic Acids | 0.20 |
| Sensimune ™ 75 (Yeast Cell Wall) | 0.15 |

Example 11

Table 8 describes certain embodiments having proportion of the composition (% of dry weight of component composition) that includes total arginine present at 1.84% or less, and in some embodiments, total arginine present at 1.21% or less, and in some embodiments, total arginine present at 1.11% or less, and in some embodiments, total arginine present at less than 1.04%, and in some embodiments, total arginine present at 1.04-1.84%.

TABLE 9

| Ingredient | w/w % |
|---|---|
| Rice, brewers | 25.00 |
| Pea, protein concentrate | 10.00 |
| Chicken Dried 10% Ash | 8.00 |
| Chicken, ground, fresh | 7.00 |
| Sorghum, whole | 6.36 |
| Chicken Meal | 6.14 |
| Pork Fat, Choice White Grease | 1.00 |
| Flax, seed, whole | 3.00 |
| Eggs, dried, granulated | 5.50 |
| Pecan Fiber | 4.80 |
| G03 Buckwheat Groats | 4.00 |
| Oat, groats | 4.00 |
| Captex 355 Medium Chained Triglyceride | 3.00 |
| Chicken, liver, digest, optimizor LDPE H | 2.00 |
| Oat, fiber | 1.50 |
| Beet, pulp, ground, fine | 1.50 |
| Lactic acid, food grade | 1.50 |
| Fish oil, TG, 18/12, NP | 1.20 |
| Flav Gen#1 + CWG | 1.00 |
| Potassium chloride | 0.30 |
| Carnitine, 1, 10% | 0.27 |
| Natural flavor, Pork, Liver, Digest, D'T | 0.25 |
| Choline chloride, liquid, 70% | 0.18 |
| Sensimune 75 (Yeast Cell Wall) | 0.15 |
| Vitamin E, oil, 29% | 0.14 |
| Taurine | 0.10 |
| Sodium chloride, iodized | 0.10 |
| Lysine, 1, hydrochloride | 0.10 |
| Mineral, premix, 2305 | 0.04 |
| Oat Fiber, Fruit, Vegetable blend | 0.04 |
| Dicalcium phosphate | 0.04 |

Example 12

Table 10 describes certain embodiments having proportion of the composition (% of dry weight of component composition) that includes total arginine present at 1.84% or less, and in some embodiments, total arginine present at 1.21% or less, and in some embodiments, total arginine present at 1.11% or less, and in some embodiments, total arginine present at less than 1.04%, and in some embodiments, total arginine present at 1.04-1.84%.

TABLE 10

| Ingredient | w/w % |
|---|---|
| Rice, Brewers | — |
| Chicken Meal | 7.00 |
| Pea, protein concentrate | 8.00 |
| Cellulose, coarse | 4.00 |
| Chicken Dried 10% Ash | 6.00 |
| Barley, pearled, cracked | 20.00 |
| Chicken, ground, fresh | 8.00 |
| Flax, seed, whole | 2.00 |
| Coconut oil preserved | 4.00 |
| Chicken, liver, digest, optimizor LDPE H | 3.00 |
| Lactic acid | 1.50 |
| Methionine, dl | 0.64 |
| Potassium chloride | 0.50 |
| Sodium chloride, iodized | 0.60 |
| Fish oil, TG, 18/12, NP | 0.50 |
| Calcium carbonate | 0.30 |
| Choline chloride, liquid, 70% | 0.25 |
| Carnitine, 1, 10% | 0.30 |
| Vitamin E, oil, 29% | 0.17 |
| Mineral, premix, 2305 | 0.08 |
| Taurine | 0.06 |
| Oat, groats | 10.00 |
| Buckwheat Groats | 6.92 |
| Pea, bran, meal | 5.00 |
| Tomato, pomace, | 5.00 |
| Beet, pulp, ground, fine | 3.00 |

Example 13

Table 11 describes certain embodiments having proportion of the composition (% of dry weight of component composition) that includes total arginine present at 1.84% or less, and in some embodiments, total arginine present at 1.21% or less, and in some embodiments, total arginine present at 1.11% or less, and in some embodiments, total arginine present at less than 1.04%, and in some embodiments, total arginine present at 1.04-1.84%.

TABLE 11

| Ingredient | w/w % | w/w % |
|---|---|---|
| Corn starch | 31.10 | 48.11 |
| Hydrolyzed chicken liver and heart | 37.00 | 32.00 |
| Soybean oil, crude, degummed | 3.60 | 4.66 |
| Cellulose, pelleted | — | 3.94 |
| Chicken, liver, digest, optimizer LDPE H | 2.00 | 2.00 |
| Lactic acid, food grade | 1.50 | 1.50 |
| Calcium carbonate | 1.22 | 1.22 |
| Dicalcium phosphate | 1.22 | 1.22 |
| Choice White Grease/Phos Acid | 1.25 | 1.00 |
| Flav Gen#1 + CWG | 1.25 | 0.75 |
| Glyceryl monostearate | 0.74 | 0.74 |
| Potassium chloride | 0.69 | 0.69 |
| Natural flavor, Pork, Liver, Digest, D'T | 0.75 | 0.50 |
| Sodium chloride, iodized | 0.44 | 0.44 |
| Choline chloride, liquid, 70% | 0.38 | 0.38 |
| Methionine, dl | 0.30 | 0.30 |
| Sodium tripolyphosphate | 0.15 | 0.15 |
| Vitamin premix | 0.12 | 0.12 |
| Mineral, premix, 2305 | 0.07 | 0.07 |
| Taurine | 0.02 | 0.02 |
| Pecan shells, ground | 7.00 | — |
| Flax seed whole brown | 3.00 | — |
| Beet pulp, ground, fine | 2.50 | — |
| Cranberry pomace | 1.00 | — |

Example 14

Table 12 describes certain embodiments having proportion of the composition (% of dry weight of component composition) that includes total arginine present at 1.84% or less, and in some embodiments, total arginine present at 1.21% or less, and in some embodiments, total arginine present at 1.11% or less, and in some embodiments, total arginine present at less than 1.04%, and in some embodiments, total arginine present at 1.04-1.84%.

TABLE 12

| Ingredient | w/w % | w/w % |
|---|---|---|
| Chicken meal | 15.36 | 15.36 |
| Rice, brewers | 8.64 | 8.64 |
| Eggs, dried, granulated | 8.00 | 8.00 |
| Corn, gluten, meal | 7.62 | 7.62 |
| Sorghum, whole | 5.00 | 5.00 |
| Choice white grease/Phos Acid | 4.00 | 4.00 |
| Palatant, 12 L, Liquid | 3.00 | 3.00 |
| Lactic acid, food grade | 1.50 | 1.50 |
| Soybean oil, crude, degummed | 1.05 | 1.05 |
| Palatant, ITE2, Dry | 1.00 | 1.00 |
| Potassium chloride | 0.89 | 0.89 |
| Sodium chloride, iodized | 0.61 | 0.61 |
| Calcium carbonate | 0.41 | 0.41 |
| Dicalcium phosphate | 0.25 | 0.25 |
| Vitamin E, oil, 29% | 0.17 | 0.17 |
| Choline chloride, liquid, 70% | 0.16 | 0.16 |
| Mineral, premix, 2305 | 0.06 | 0.06 |
| Tryptophan | 0.04 | 0.04 |
| Taurine | 0.04 | 0.04 |
| Cellulose, pelleted | — | 1.50 |
| Corn, yellow, whole | 26.00 | 40.00 |
| Pecan shells, ground | 7.00 | — |
| Flax seed whole brown | 3.00 | — |
| Beet pulp, ground, fine | 2.50 | 0.50 |
| Cranberry pomace | 1.00 | — |

Example 15

Table 13 describes certain embodiments having proportion of the composition (% of dry weight of component composition) that includes total arginine present at 1.84% or less, and in some embodiments, total arginine present at 1.21% or less, and in some embodiments, total arginine present at 1.11% or less, and in some embodiments, total arginine present at less than 1.04%, and in some embodiments, total arginine present at 1.04-1.84%.

TABLE 13

| Ingredient | w/w % | w/w % | w/w % | w/w % | w/w % |
|---|---|---|---|---|---|
| Protein | 19.7 | 24.7 | 24.7 | 24.8 | 24.8 |
| Fat | 20.6 | 16.9 | 16.9 | 22.0 | 22.0 |
| Carbohydrate | 53.8 | 51.0 | 51.0 | 46.3 | 27.6 |
| Crude Fiber | 0.37 | 2.6 | 2.6 | 1.4 | 21.0 |

TABLE 14

| COMMON NAME Genus species Short name | Dry Matter (%) | Crude Protein (%) | Arginine (%) |
|---|---|---|---|
| BARLEY *Hordeum vulgare* | | | |
| grain, | 89 | 13.0 | 0.66 |
| grain, Pacific Coast | 89 | 10.1 | 0.54 |
| BLOOD, ANIMAL | | | |
| fresh | — | — | — |
| meal spray dehydrated | 93 | 95.6 | 4.10 |
| BONE, ANIMAL | | | |
| meal steamed | 90 | 11.4 | 1.79 |
| phosphate | 98 | — | — |
| BREAD *Triticum aestivum* | | | |
| dehydrated (wheat) | 95 | 13.0 | — |
| BUTTERMILK *Bos taurus* | | | |
| dehydrated | 92 | 34.4 | 1.17 |
| CANOLA *Brassica napus-Brassica campestris* | | | |
| seeds, meal prepressed, solv extd, low erucic acid, low glucosinolates | 93 | 40.9 | 2.49 |
| CASEIN | | | |
| dehydrated | 93 | 93.8 | 3.88 |
| CATTLE *Bos taurus* | | | |
| chucks | 39 | 47.7 | — |
| lips, fresh | 30 | 80.0 | — |
| livers, fresh | 28 | 69.6 | 3.56 |
| lung, fresh | 24 | 65.0 | 3.10 |
| spleens, fresh | 24 | 88.7 | — |
| tripe, dressed (lime treated) | 33 | 46.1 | 5.50 |
| udders, fresh | 20 | 58.6 | — |
| CORN, DENT YELLOW *Zea mays indentata* | | | |
| distillers grains w solubles dehydrated | 93 | 29.3 | 1.05 |
| distillers solubles, dehydrated | 92 | 31.0 | 1.14 |
| germ, meal wet milled solv extd | 92 | 22.6 | 1.43 |
| gluten, meal 60% | 90 | 88.9 | 2.14 |
| grain, flaked | 90 | 11.2 | 0.49 |
| hominy feed | 90 | 11.1 | 0.52 |
| grain | 89 | 9.9 | 0.50 |
| COTTON *Gossypium* spp | | | |
| seeds, meal prepressed solv extd, 41% protein | 90 | 46.0 | 5.10 |
| seeds, meal solv extd, 41% protein | 91 | 45.4 | 4.66 |
| seeds wo/hulls, meal prepressed solv extd, 50% protein | 93 | 54.0 | 5.20 |
| CRAB *Callinecles sapidus-Cancer* spp-*Paralithodes camschiatica* | | | |
| cannery residue, meal | 92 | 35.0 | 1.80 |
| FISH, ALEWIFE *Pomotobus pseudoharengus* | | | |
| meal mech extd | 90 | 69.4 | 4.96 |
| whole, fresh | 26 | 75.8 | — |
| FISH, ANCHOVY *Engraulis ringen* | | | |
| meal mech extd | 92 | 69.8 | 3.98 |
| FISH, CARP *Cyprinus carpio* | | | |
| meal mech extd | 90 | 58.6 | — |
| whole, fresh | 31 | 61.9 | — |
| FISH, CATFISH *Ictalurus* spp | | | |
| meal, mech extd | 94 | 55.3 | — |
| whole, fresh | 22 | — | — |
| FISH, COD *Gadus morrhua-Gadus macrocephalus* | | | |
| meal, mech extd | 84 | 73.1 | — |
| whole, fresh | — | — | — |
| FISH, FLOUNDER Bothidae (family)-Pleuronectidae (family) | | | |
| whole, fresh | 17 | 88.2 | — |

TABLE 14-continued

| COMMON NAME Genus species<br>Short name | Dry Matter<br>(%) | Crude Protein<br>(%) | Arginine<br>(%) |
|---|---|---|---|
| FISH, HADDOCK *Melanogrammus aeglefinus* | | | |
| whole, fresh | 10 | 93.8 | — |
| FISH, HAKE *Merluccius* spp-*Urophycis* spp | | | |
| whole, boiled | 26 | 57.8 | |
| whole, boiled acidified | 25 | | |
| whole, fresh | 20 | 50.6 | — |
| FISH, HERRING *Clupea harengus* | | | |
| meal, mech extd | 93 | 77.7 | 5.20 |
| whole, fresh | 29 | 63.1 | — |
| FISH, MACKEREL *Scomber scrombus* | | | |
| Atlantic, whole, fresh | 28 | 48.7 | — |
| FISH, MACKEREL *Scomber japonicus* | | | |
| Pacific, whole, fresh | 30 | 72.5 | — |
| FISH, MENHADEN *Brevoartia tyrannus* | | | |
| meal, mech extd | 92 | 65.8 | 4.12 |
| FISH, REDFISH *Sciaenops occellata* | | | |
| meal, mech extd | 93 | 61.0 | 4.36 |
| FISH, ROCKFISH *Sebastodes* spp | | | |
| whole, fresh | 21 | 89.6 | — |
| FISH, SALMON *Oncorhynchus* spp-*Salmo* spp | | | |
| meal, mech extd | 94 | 65.3 | 5.50 |
| whole, fresh | 32 | 66.2 | — |
| FISH, SARDINE *Clupea* spp-*Sardinops* spp *Osmerus* spp | | | |
| meal, mech extd | 93 | 70.0 | 2.93 |
| FISH, SMELT Soleidae (family) | | | |
| whole, fresh | 21 | 89.6 | — |
| FISH, TUNA *Thunnus thynnus-Thunnus albacares* | | | |
| cannery residue | 81 | 55.5 | 3.65 |
| meal, mech extd | 93 | 63.6 | 3.44 |
| FISH, TURBOT *Psetta maxima* | | | |
| whole, fresh | 25 | 57.3 | — |
| FISH, WHITE Gadidae (family)-Lophidae (family)-Rajidae (family) | | | |
| meal, mech extd | 93 | 68.4 | 4.42 |
| FISH, WHITING *Gadus merlangus* | | | |
| whole, fresh | 23 | 69.9 | — |
| FISH | | | |
| livers, mech extd | 93 | 67.7 | |
| racks, dehydrated grad (bones w heads) | — | — | |
| solubles, condensed | 51 | 61.8 | — |
| solubles, dehydrated | 92 | 69.1 | — |
| FLAX *Linum usitatissimum* | | | |
| seeds, meal solv extd (linseed meal) | 90 | 38.4 | 3.25 |
| HAMBURGER *Bos taurus* | | | |
| fresh, 10% fat | 38 | 65.3 | 2.21 |
| fresh, 20% fat | 39 | 45.0 | — |
| HORSE *Equus caballus* | | | |
| meat, fresh | 31 | 63.6 | — |
| meal w bone fresh | 36 | 51.4 | — |
| LIVER, ANIMAL | | | |
| meat, dehydrated | 92 | 71.3 | 4.50 |
| MEAT, ANIMAL | | | |
| meal, rendered | 92 | 50.1 | 4.05 |
| w blood, w bone, meal tankage rendered | 93 | 50.2 | 3.03 |
| w bone, meal rendered | 93 | 53.9 | 3.80 |

TABLE 14-continued

| COMMON NAME Genus species<br>Short name | Dry Matter (%) | Crude Protein (%) | Arginine (%) |
|---|---|---|---|
| MILK | | | |
| dehydrated (cattle) | 96 | 26.6 | 0.96 |
| fresh (cattle) | 12 | 26.7 | — |
| skimmed dehydrated (cattle) | 94 | 35.4 | — |
| skimmed fresh (cattle) | 10 | 31.2 | — |
| cottage cheese | 21 | 81.0 | — |
| whey albumin (cattle) | 92 | 52.5 | — |
| MILLET, FOXTAIL *Setaria italica* | | | |
| grain | 89 | 12.8 | 0.72 |
| MOLASSES | | | |
| beet sugar, molasses, mt 48% | 78 | 8.5 | — |
| invert sugar mt 79.5 degrees brix, sugar cane, molasses dehydrated | 94 | 10.3 | — |
| sugar cane, molasses dehydrated, mt 46% invert, sugar mt 79.5 degrees brix | 74 | 5.8 | — |
| OATS *Avena sativa* | | | |
| cereal by-product, lt 4% fiber (feeding oat meal) (oat middlings) | 91.0 | 16.3 | 0.89 |
| grain | 89 | 12.8 | 0.90 |
| groats | 90 | 17.6 | 0.99 |
| hulls | 92 | 5.2 | 0.16 |
| PEA *Pisum* spp | | | |
| seeds | 90 | 26.4 | 1.56 |
| PEANUT *Arachis hypogaca* | | | |
| kernels, meal solv extd (peanut meal) | 93 | 54.5 | 5.91 |
| POTATO *Solanum tuberosum* | | | |
| tubers, dehydrated | 91 | 8.9 | 0.28 |
| POULTRY *Gallus domesticus* | | | |
| heads, fresh | 33 | 57.6 | — |
| broilers, whole fresh | — | — | — |
| eggs, fresh whole | 30 | 42.6 | 2.90 |
| eggs, fresh white | 13 | 87.1 | 4.96 |
| feet fresh | 33 | 54.5 | — |
| gizzards fresh | 25 | 80.4 | — |
| by-products, fresh (viscera with feet and heads) | — | — | — |
| by-product, meal rendered (viscera with feet and heads) | 93 | 62.4 | 4.30 |
| hens, whole fresh | — | — | — |
| chicken viscera | 26 | 54.4 | — |
| POULTRY FEATHERS | | | |
| hydrolyzed meal | 93 | 92.9 | 5.83 |
| RICE *Orzya sativa* | | | |
| bran w germ (rice bran) | 91 | 14.2 | 0.98 |
| grain | 89 | 8.6 | 0.65 |
| groats, polished | 89 | 8.2 | 0.50 |
| polishings | 90 | 13.6 | 0.87 |
| RYE *Secate cereale* | | | |
| grain | 88 | 13.7 | 0.60 |
| SEAWEED, KELP | | | |
| Laminariales order, Fucales order | 91 | 7.1 | — |
| SESAME *Sesamum indicum* | | | |
| seeds, meal mech extd | 93 | 47.1 | 5.30 |
| SHRIMP *Pandalus* spp-*Panacus* spp | | | |
| cannery residual meal (shrimp meal) | 90 | 43.0 | 2.58 |
| SORGHUM *vulgare* | | | |
| grain | 90 | 10.0 | 0.40 |
| SOYBEAN *Glycine max* | | | |
| seeds, meal mech extd | 89 | 49.4 | 3.69 |
| seeds wo hulls, meal mech extd | 90 | 53.9 | 3.80 |
| flour, concentrate 70% protein | 93 | 90.4 | 7.20 |
| flour, oil residue solvent extd | 93 | 55.3 | 4.58 |

TABLE 14-continued

| COMMON NAME Genus species Short name | Dry Matter (%) | Crude Protein (%) | Arginine (%) |
|---|---|---|---|
| isolate 90% protein | 96 | 94.0 | 3.80 |
| seeds, heat processed | 90 | 41.1 | 3.11 |
| SUCROSE | | | |
| sucrose | 99 | — | — |
| SUNFLOWER *Helianthus* spp. | | | |
| seeds wo hulls, meal mech extd | 93 | 43.7 | 3.66 |
| seeds wo hulls, meal solv extd | 93 | 43.8 | 3.76 |
| SWINE *Sus scrofa* | | | |
| livers fresh | 30.5 | 69.8 | 3.69 |
| lungs fresh | — | — | — |
| TOMATO *Lycopersicon esculentum* | | | |
| pomace dehydrated | 92 | 23.0 | 1.30 |
| TURKEY *Meleagris gallopavo* | | | |
| mature birds, offal fresh | — | — | — |
| young heads, offal fresh | — | — | — |
| viscera fresh | 31 | 43.4 | — |
| WHALE *balaena glacialis-Balaenoptera* spp.-*Physter catadon* | | | |
| meat fresh | 29 | 70.8 | — |
| WHEAT *Triticum aestivum* | | | |
| bran | 90 | 17.4 | 1.0 |
| flour, hard red spring | 89 | 14.4 | 0.55 |
| flour, lt 2% fiber | 88 | 15.5 | 0.52 |
| germ meal | 88 | 27.6 | 1.65 |
| grain | 89 | 14.7 | 0.66 |
| grain, hard red spring | 88 | 16.2 | 0.68 |
| grain, hard red winter | 87 | 16.2 | 0.83 |
| grain, screenings | 89 | 14.9 | 0.60 |
| grain, soft red winter | 88 | 12.9 | 0.62 |
| grain, soft white winter | 89 | 11.5 | 0.55 |
| grits | 90 | 12.7 | — |
| mill run, lt 9.5% fiber | 90 | 16.7 | 0.59 |
| red dog, lt 4.5% fiber | 88 | 17.4 | 0.84 |
| shorts, lt 7.0% fiber | 88 | 18.7 | 1.08 |
| middlings, lt 9.5% fiber | 88 | 17.6 | — |
| WHEAT DURUM *Triticum durum* | | | |
| grain | 88 | 15.6 | 0.52 |
| WHEY *Bos taurus* | | | |
| dehydrated | 93 | 12.9 | 0.32 |
| low lactose, dehydrated (dried whey product) | 91 | 17.0 | 1.14 |
| YEAST *Saccaromyces cerevisae* | | | |
| brewers dehydrated | 93 | 47.7 | 2.24 |
| primary dehydrated | 93 | 51.8 | — |
| YEAST *Candida utilis* | | | |
| petroleum solv extd dehydrated | 92 | 51.1 | — |
| YEAST *Torulopsis utilis* | | | |
| torula dehydrated | 93 | 50.8 | 2.80 |

The invention claimed is:

1. A method of reducing risk of hypothyroidism in a canine subject comprising:
   identifying the canine subject as being a canine subject with an increased likelihood of developing hypothyroidism, wherein identifying the canine subject comprises analyzing a biological sample obtained from the canine subject for the presence of either:
      one or two copies of minor allele T of SNP Affx-206229307; or
      one or two copies of minor allele A of SNP Affx-206560187; or
      one or two copies of minor allele T of SNP Affx-206229307 and one or two copies of minor allele A of SNP Affx-206560187;
      wherein the presence of one or two copies of minor allele T of SNP Affx-206229307; or one or two copies of minor allele A of SNP Affx-206560187; or one or two copies of minor allele T of SNP Affx-206229307 and one or two copies of minor allele A of SNP Affx-206560187 indicates that the canine subject has an increased likelihood of developing hypothyroidism; and
   feeding the canine subject a daily diet of a low arginine nutritional composition, wherein the low arginine nutritional composition contains less than 1.11% arginine per total daily nutritional intake.

2. The method of claim 1, wherein the sample is a genomic DNA sample.

3. The method of claim 2, wherein the sample is obtained from blood, saliva, follicle root, nasal swab or oral swab of the canine subject.

4. The method of claim 1, wherein the sample is analyzed by performing at least one nucleic acid analysis technique selected from: DNA sequencing, restriction enzyme digest, polymerase chain reaction (PCR), hybridization, real-time PCR, reverse transcriptase PCR, or ligase chain reaction.

5. The method of claim 1, wherein the sample is analyzed by performing at least one nucleic acid analysis technique selected from: analysis using a whole genome SNP chip, single-stranded conformational polymorphism (SSCP) assay, restriction fragment length polymorphism (RFLP), automated fluorescent sequencing; clamped denaturing gel electrophoresis (CDGE); denaturing gradient gel electrophoresis (DGGE), mobility shift analysis, restriction enzyme analysis, heteroduplex analysis, chemical mismatch cleavage (CMC), RNase protection assays, use of polypeptides that recognize nucleotide mismatches, allele-specific PCR, sequence analysis, and SNP genotyping.

6. The method of claim 1, wherein the sample is analyzed by performing at least one nucleic acid analysis technique selected from: hybridization-based methods, enzyme-based methods, post-amplification methods based on physical properties of DNA, and sequencing methods.

7. The method of claim 1, wherein the sample is analyzed by performing at least one nucleic acid analysis technique selected from: hybridization-based methods selected from the group consisting of dynamic allele-specific hybridization, molecular beacon methods and SNP microarrays; enzyme-based methods selected from the group consisting of restriction fragment length polymorphism (RFLP), PCR-based methods, Flap endonuclease, primer extension methods, 5'-nuclease and oligonucleotide ligation assay; post-amplification methods based on physical properties of DNA selected from the group consisting of single strand conformation polymorphism, temperature gradient gel electrophoresis, denaturing high performance liquid chromatography, high-resolution amplicon melting, DNA mismatch-binding proteins, SNPlex, and surveyor nuclease assay; and sequencing methods.

8. The method of claim 1 wherein the canine subject is fed a daily diet of a low arginine nutritional composition that contains less than 1.04% arginine per total daily nutritional intake.

* * * * *

SEQUENCE LISTING

<160> NUMBER OF SEQ ID NOS: 2

<210> SEQ ID NO 1
<211> LENGTH: 200
<212> TYPE: DNA
<213> ORGANISM: Canis familiaris

<400> SEQUENCE: 1
tcaaattccc attcttggca acaagcaccc accaccctc tgcctgacac attctgctct      60
cttccttcgt tcccttcttg catgaccgcc ccacacaccg ycttcattga gcagatataa     120

```
ttgccccttc tttaaacctc aatccaggga cccctgggtg gttcagtggt gagtgtctgc    180
ctttggctca gggtgtaatc                                                200

<210> SEQ ID NO 2
<211> LENGTH: 201
<212> TYPE: DNA
<213> ORGANISM: Canis familiaris

<400> SEQUENCE: 2
ccaccttttc ttccttttgt tcagttattt taattctgtc ttcatcaaag cccatcccaa     60
gaataaggga gtatattgca gttttgcgat taacgcgagc rctagaagaa acacttctat    120
gtcagcaaaa tgtccccgtg ttctgggaga gaactttgaa ggaggacggg ggaagtgcag    180
cagtgtttac tgacagtcca g                                              201
```